US006177249B1

(12) United States Patent
Kwok et al.

(10) Patent No.: US 6,177,249 B1
(45) Date of Patent: Jan. 23, 2001

(54) METHOD FOR NUCLEIC ACID ANALYSIS USING FLUORESCENCE RESONANCE ENERGY TRANSFER

(75) Inventors: Pui-Yan Kwok, Clayton; Xiangning Chen, St. Louis, both of MO (US)

(73) Assignee: Washington University, St. Louis, MO (US)

( * ) Notice: Under 35 U.S.C. 154(b), the term of this patent shall be extended for 0 days.

(21) Appl. No.: 09/295,026

(22) Filed: Apr. 20, 1999

Related U.S. Application Data

(63) Continuation of application No. 08/767,979, filed on Dec. 17, 1996, now Pat. No. 5,945,283.
(60) Provisional application No. 60/008,743, filed on Dec. 18, 1995, now abandoned.

(51) Int. Cl.[7] .......................... C12Q 1/68; G01N 33/566
(52) U.S. Cl. .................................. 435/6; 436/501
(58) Field of Search .................... 435/6; 436/501

(56) References Cited

U.S. PATENT DOCUMENTS

| 4,828,979 | 5/1989 | Klevan et al. . |
| 4,883,750 | 11/1989 | Whiteley et al. . |
| 4,988,617 | 1/1991 | Landegren et al. . |
| 5,242,794 | 9/1993 | Whiteley et al. . |
| 5,538,848 | 7/1996 | Livak et al. . |
| 5,945,283 | * 8/1999 | Kwok et al. ........................ 435/6 |

FOREIGN PATENT DOCUMENTS

| 0 070 685 A2 | 1/1983 | (EP) . |
| 0 229 943 A2 | 7/1987 | (EP) . |
| 0 601 889 A2 | 6/1994 | (EP) . |

OTHER PUBLICATIONS

Cardullo et al., Detection of nucleic acid hybridization by nonradiative fluorescence resonance energy transfer, *Proc. Natl. Acad. Sci. USA* 85:8790–8794 (1988).
Gibson et al., A Novel Method for Real Time Quantitative RT–PCR, *Genome Research* 6:995–1001 (1996).
Heid et al., Real Time Quantitative PCR, *Genome Research* 6:986–994 (1996).

(List continued on next page.)

* cited by examiner

Primary Examiner—Jezia Riley
(74) Attorney, Agent, or Firm—Howell & Haferkamp, LC

(57) ABSTRACT

A method for detecting the presence of a target nucleotide or sequence of nucleotides in a nucleic acid is disclosed. The method is comprised of forming an oligonucleotide labeled with two fluorophores on the nucleic acid target site. The doubly labeled oligonucleotide is formed by addition of a singly labeled dideoxynucleoside triphosphate to a singly labeled polynucleotide or by ligation of two singly labeled polynucleotides. Detection of fluorescence resonance energy transfer upon denaturation indicates the presence of the target. Kits are also provided. The method is particularly applicable to genotyping.

10 Claims, 8 Drawing Sheets

(1 of 8 Drawing Sheet(s) Filed in Color)

OTHER PUBLICATIONS

Holland et al., Detection of specific polymerase chain reaction product by utilizing the 5'→3' exonuclease activity of Thermus aquatics DNA polymerase, *Proc. Natl. Acad. Sci. USA* 88:7276–7280 (1991).

Landegren et al., A Ligase–Mediated Gene Detection Technique, *Science* 241:1077–1080 (1988).

Lee et al., Allelic discrimination by nick–translation PCR with fluorogenic probes, *Nucleic Acids Research* 21(16):3761–3766 (1993).

Livak et al., Oligonucleotides with Fluorescent Dyes at Opposite Ends Provide a Quenched Probe System Useful for Detecting PCR Product and Nucleic Acid Hybridization, *PCR Method and Applications* 4:357–362 (1995).

Nickerson et al., Automated DNA diagnostics using an ELISA–based oligonucleotide ligation assay, *Proc. Natl. Acad. Science USA* 87:8923–8927 (1990).

Nikiforov et al., Genetic Bit Analysis: a solid phase method for typing single nucleotide polymorphisms, *Nucleic Acids Research* 22:4167–4175 (1994).

Tyagi et al., Molecular Beacons: Probes that Fluoresce upon Hybridization, *Nature Biotechnology* 14:303–308 (1996).

Yershov et al., DNA analysis and diagnostics on oligonucleotide microchips, *Proc. Natl. Acad. Sci. USA* 93:4913–4918 (1996).

SEQUENCE LISTING (1) GENERAL INFORMATION:

(iii) NUMBER OF SEQUENCES: 34

(2) INFORMATION FOR SEQ ID NO: 1:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "s14102-40A; SYNTHETIC FORTY (iii) HYPOTHETICAL: NO (iv) ANTI-SENSE: NO (xi) SEQUENCE DESCRIPTION: SEQ ID NO: 1:

ATTTTACAAA AATAAAACAA AGAAACCACT AAGCCATAAA    40

(2) INFORMATION FOR SEQ ID NO: 2:

(i) SEQUENCE CHARACTERISTICS:
      (A) LENGTH: 40 base pairs
      (B) TYPE: nucleic acid (C) STRANDEDNESS: single
        (D) TOPOLOGY: linear (ii) MOLECULE TYPE: other nucleic acid
        (A) DESCRIPTION: /desc = "s14102-40C; SYNTHETIC FORTY (iii) HYPOTHETICAL: NO (iv) ANTI-SENSE: NO (xi) SEQUENCE DESCRIPTION: SEQ ID NO: 2:

ATTTTACAAA AATAAAACAA CGAAACCACT AAGCCATAAA                                   40

(2) INFORMATION FOR SEQ ID NO: 3:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "s14102-40G; SYNTHETIC FORTY (iii) HYPOTHETICAL: NO (iv) ANTI-SENSE: NO (xi) SEQUENCE DESCRIPTION: SEQ ID NO: 3:

ATTTTACAAA AATAAAACAA GGAAACCACT AAGCCATAAA                                   40

(2) INFORMATION FOR SEQ ID NO: 4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "s14102-40T; SYNTHETIC FORTY (iii) HYPOTHETICAL: NO (iv) ANTI-SENSE: NO (xi) SEQUENCE DESCRIPTION: SEQ ID NO: 4:

ATTTTACAAA AATAAAACAA TGAAACCACT AAGCCATAAA                                   40

(2) INFORMATION FOR SEQ ID NO: 5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "S14102-F; SYNTHETIC (iii) HYPOTHETICAL: NO (iv) ANTI-SENSE: NO (ix) FEATURE:
        (A) NAME/KEY: misc_feature
        (B) LOCATION: 1
        (D) OTHER INFORMATION: /note= "FLUORESCEIN LABELED
            THYMIDINE"

(xi) SEQUENCE DESCRIPTION: SEQ ID NO: 5:

NTTATGGCTT AGTGGTTTC                                                          19

(2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "D18S8p1; SYNTHETIC PCR (iii) HYPOTHETICAL: NO (iv) ANTI-SENSE: NO (xi) SEQUENCE DESCRIPTION: SEQ ID NO: 6:

TTGCACCATG CTGAAGATTG T                                      21

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "D18S8p2; SYNTHETIC PCR (iii) HYPOTHETICAL: NO (iv) ANTI-SENSE: NO (xi) SEQUENCE DESCRIPTION: SEQ ID NO: 7:

ACCCTCCCCC TGATGACTTA                                        20

(2) INFORMATION FOR SEQ ID NO: 8:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "D18S8 ALLELE A; DNA (iii) HYPOTHETICAL: NO (iv) ANTI-SENSE: NO (xi) SEQUENCE DESCRIPTION: SEQ ID NO: 8:

AGGAGAATTG CTTGAACCCA GGAGGCAGAG CTTGCAGTGA                    40

(2) INFORMATION FOR SEQ ID NO: 9:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "D18S8 ALLELE G; DNA (iii) HYPOTHETICAL: NO (iv) ANTI-SENSE: NO (xi) SEQUENCE DESCRIPTION: SEQ ID NO: 9:

AGGAGAATTG CTTGAACCCG GGAGGCAGAG CTTGCAGTGA						40

(2) INFORMATION FOR SEQ ID NO: 10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "D18S8 PROBE; SYNTHETIC (iii) HYPOTHETICAL: NO (iv) ANTI-SENSE: NO (ix) FEATURE:
        (A) NAME/KEY: misc_feature
        (B) LOCATION: 1
        (D) OTHER INFORMATION: /note= "N REPRESENTS 5' FLUORESCEIN
            LABELED CYTOSINE;"

(ix) FEATURE:
        (A) NAME/KEY: misc_feature
        (B) LOCATION: 1

(xi) SEQUENCE DESCRIPTION: SEQ ID NO: 10:

NACTGCAAGC TCTGCCTCC						19

(2) INFORMATION FOR SEQ ID NO: 11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DXS17p1; SYNTHETIC PCR (iii) HYPOTHETICAL: NO (iv) ANTI-SENSE: NO (xi) SEQUENCE DESCRIPTION: SEQ ID NO: 11:

GCAATTATCT GTATTACTTG AAT						23

(2) INFORMATION FOR SEQ ID NO: 12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DXS17p2; SYNTHETIC PCR (iii) HYPOTHETICAL: NO (iv) ANTI-SENSE: NO (xi) SEQUENCE DESCRIPTION: SEQ ID NO: 12:

GGTACATGAC AATCTCCCAA TAT						23

(2) INFORMATION FOR SEQ ID NO: 13:

(i) SEQUENCE CHARACTERISTICS:
        (A) LENGTH: 39 base pairs
        (B) TYPE: nucleic acid
        (C) STRANDEDNESS: single

```
        (D) TOPOLOGY: linear (ii) MOLECULE TYPE: other nucleic acid
        (A) DESCRIPTION: /desc = "DXS17 ALLELE A; NUCLEOTIDE (iii) HYPOTHETICAL: NO (iv) ANTI-SENSE: NO (xi) SEQUENCE DESCRIPTION: SEQ ID NO: 13:

ATTGGATTAT TTGTAACTCA AAGGATAAGT GCATAAGGG                                   39

(2) INFORMATION FOR SEQ ID NO: 14:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DXS17 ALLELE G; NUCLEOTIDE (iii) HYPOTHETICAL: NO (iv) ANTI-SENSE: NO (xi) SEQUENCE DESCRIPTION: SEQ ID NO: 14:

ATTGGATTAT TTGTAACTCG AAGGATAAGT GCATAAGGG                                   39

(2) INFORMATION FOR SEQ ID NO: 15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DXS17 PROBE; SYNTHETIC (iii) HYPOTHETICAL: NO (iv) ANTI-SENSE: NO (ix) FEATURE:
        (A) NAME/KEY: misc_feature
        (B) LOCATION: 1
        (D) OTHER INFORMATION: /note= "N REPRESENTS 5'END
            FLUORESCEIN LABELED CYTOSINE;"

(xi) SEQUENCE DESCRIPTION: SEQ ID NO: 15:

NCCTTATGCA CTTATCCTT                                                         19

(2) INFORMATION FOR SEQ ID NO: 16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "MEN11p1; PCR PRIMER USED (iii) HYPOTHETICAL: NO (iv) ANTI-SENSE: NO (xi) SEQUENCE DESCRIPTION: SEQ ID NO: 16:

CCTCTGCGGT GCCAAGCCTC                                                        20
```

(2) INFORMATION FOR SEQ ID NO: 17:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "MEN11p2; PCR PRIMER USED (iii) HYPOTHETICAL: NO (iv) ANTI-SENSE: NO (xi) SEQUENCE DESCRIPTION: SEQ ID NO: 17:

CACCGGAAGA GGAGTAGCTG                                               20

(2) INFORMATION FOR SEQ ID NO: 18:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "MEN C634F; SYNTHETIC (iii) HYPOTHETICAL: NO (iv) ANTI-SENSE: NO (ix) FEATURE:
       (A) NAME/KEY: misc_feature
       (B) LOCATION: 1
       (D) OTHER INFORMATION: /note= "N REPRESENTS 5'END
           FLUORESCEIN LABELED CYTOSINE;"

(xi) SEQUENCE DESCRIPTION: SEQ ID NO: 18:

NCACTGTGCG ACGAGCTGT                                                19

(2) INFORMATION FOR SEQ ID NO: 19:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "CF508p1; PCR PRIMER USED (iii) HYPOTHETICAL: NO (iv) ANTI-SENSE: NO (xi) SEQUENCE DESCRIPTION: SEQ ID NO: 19:

GTGCATAGCA GAGTACCTGA AACAGGAAGT A                                  31

(2) INFORMATION FOR SEQ ID NO: 20:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "CF508p2; PCR PRIMER USED (iii) HYPOTHETICAL: NO (iv) ANTI-SENSE: NO (xi) SEQUENCE DESCRIPTION: SEQ ID NO: 20:

TGATCCATTC ACAGTAGCTT ACCCATAGAG G                                               31

(2) INFORMATION FOR SEQ ID NO: 21:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "CF508F25; SYNTHETIC DNA (iii) HYPOTHETICAL: NO (iv) ANTI-SENSE: NO (ix) FEATURE:
            (A) NAME/KEY: misc_feature
            (B) LOCATION: 1
            (D) OTHER INFORMATION: /note= "N REPRESENTS 5'END
                FLUORESCEIN LABELED CYTOSINE;"

(xi) SEQUENCE DESCRIPTION: SEQ ID NO: 21:

NTGGCACCAT TAAAGAAAAT ATCAT                                                      25

(2) INFORMATION FOR SEQ ID NO: 22:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DONOR SEQ; SYNTHETIC (iii) HYPOTHETICAL: NO (iv) ANTI-SENSE: NO (xi) SEQUENCE DESCRIPTION: SEQ ID NO: 22:

TTGTTTTATT TTTGTAAAAT                                                            20

(2) INFORMATION FOR SEQ ID NO: 23:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "ACCEPTOR SEQ A; SYNTHETIC (iii) HYPOTHETICAL: NO (iv) ANTI-SENSE: NO (xi) SEQUENCE DESCRIPTION: SEQ ID NO: 23:

TTTATGGCTT AGTGGTTTCA                                                            20

(2) INFORMATION FOR SEQ ID NO: 24:

(i) SEQUENCE CHARACTERISTICS:
            (A) LENGTH: 20 base pairs
            (B) TYPE: nucleic acid

```
        (C) STRANDEDNESS: single
        (D) TOPOLOGY: linear (ii) MOLECULE TYPE: other nucleic acid
        (A) DESCRIPTION: /desc = "ACCEPTOR SEQ G; SYNTHETIC (iii) HYPOTHETICAL: NO (iv) ANTI-SENSE: NO (xi) SEQUENCE DESCRIPTION: SEQ ID NO: 24:

TTTATGGCTT AGTGGTTTCG                                                    20

(2) INFORMATION FOR SEQ ID NO: 25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "s14102p1; SYNTHETIC PCR (iii) HYPOTHETICAL: NO (iv) ANTI-SENSE: NO (xi) SEQUENCE DESCRIPTION: SEQ ID NO: 25:

CAGTATGCTC ACAAAGCC                                                      18

(2) INFORMATION FOR SEQ ID NO: 26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "a14102p2; SYNTHETIC PCR (iii) HYPOTHETICAL: NO (iv) ANTI-SENSE: NO (xi) SEQUENCE DESCRIPTION: SEQ ID NO: 26:

CTCATATTCA CATCTCTCCG                                                    20

(2) INFORMATION FOR SEQ ID NO: 27:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DXS17 COMMON PROBE;

(iii) HYPOTHETICAL: NO (iv) ANTI-SENSE: NO (ix) FEATURE:
        (A) NAME/KEY: misc_feature
        (B) LOCATION: 19
        (D) OTHER INFORMATION: /note= "N REPRESENTS 3'END
            FLUORESCEIN LABELED THYMIDINE;"

(xi) SEQUENCE DESCRIPTION: SEQ ID NO: 27:

GAGTTACAAA TAATCCAAN                                                     19
```

(2) INFORMATION FOR SEQ ID NO: 28:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DXS17 ALLELIC PROBE 1;

(iii) HYPOTHETICAL: NO (iv) ANTI-SENSE: NO (ix) FEATURE:
       (A) NAME/KEY: misc_feature
       (B) LOCATION: 1
       (D) OTHER INFORMATION: /note= "5' END RHODAMINE LABELED
           THYMIDINE;"

(xi) SEQUENCE DESCRIPTION: SEQ ID NO: 28:

NCCTTATGCA CTTATCCTTT                                             20

(2) INFORMATION FOR SEQ ID NO: 29:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DXS17 ALLELIC PROBE 2;

(iii) HYPOTHETICAL: NO (iv) ANTI-SENSE: NO (ix) FEATURE:
       (A) NAME/KEY: misc_feature
       (B) LOCATION: 1
       (D) OTHER INFORMATION: /note= "5' END TEXAS RED LABELED
           CYTOSINE;"

(xi) SEQUENCE DESCRIPTION: SEQ ID NO: 29:

NCCTTATGCA CTTATCCTTC                                             20

(2) INFORMATION FOR SEQ ID NO: 30:

(i) SEQUENCE CHARACTERISTICS:
       (A) LENGTH: 40 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "S14102 ALLELE T; A PORTION (iii) HYPOTHETICAL: NO (iv) ANTI-SENSE: NO (xi) SEQUENCE DESCRIPTION: SEQ ID NO: 30:

ATTTTACAAA AATAAAACAA TGAAACCACT AAGCCATAAA                       40

(2) INFORMATION FOR SEQ ID NO: 31:

(i) SEQUENCE CHARACTERISTICS:
       (A) LENGTH: 40 base pairs
       (B) TYPE: nucleic acid (C) STRANDEDNESS: single
        (D) TOPOLOGY: linear (ii) MOLECULE TYPE: other nucleic acid
        (A) DESCRIPTION: /desc = "S14102 ALLELE C; HUMAN (iii) HYPOTHETICAL: NO (iv) ANTI-SENSE: NO (xi) SEQUENCE DESCRIPTION: SEQ ID NO: 31:

ATTTTACAAA AATAAAACAA CGAAACCACT AAGCCATAAA                40

(2) INFORMATION FOR SEQ ID NO: 32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "S14102 COMMON PROBE;

(iii) HYPOTHETICAL: NO (iv) ANTI-SENSE: NO (ix) FEATURE:
        (A) NAME/KEY: misc_feature
        (B) LOCATION: 20
        (D) OTHER INFORMATION: /note= "N AT POSITION 20 IS
            FLUORESCEIN LABELED THYMIDINE;"

(xi) SEQUENCE DESCRIPTION: SEQ ID NO: 32:

TTGTTTTATT TTTGTAAAAN                                     20

(2) INFORMATION FOR SEQ ID NO: 33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "S14102 ALLELIC PROBE 1;

(iii) HYPOTHETICAL: NO (iv) ANTI-SENSE: NO (ix) FEATURE:
        (A) NAME/KEY: misc_feature
        (B) LOCATION: 1
        (D) OTHER INFORMATION: /note= "N REPRESENTS 5'END
            RHODAMINE LABELED THYMIDINE;"

(xi) SEQUENCE DESCRIPTION: SEQ ID NO: 33:

NTTATGGCTT AGTGGTTTCA                                     20

(2) INFORMATION FOR SEQ ID NO: 34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "S14102 ALLELIC PROBE 2;

(iii) HYPOTHETICAL: NO

-continued

```
    (iv) ANTI-SENSE: NO (ix) FEATURE:
         (A) NAME/KEY: misc_feature
         (B) LOCATION: 1
         (D) OTHER INFORMATION: /note= "N REPRESENTS 5'END TEXAS
             RED LABELED THYMIDINE;"

(xi) SEQUENCE DESCRIPTION: SEQ ID NO: 34:

NTTATGGCTT AGTGGTTTCG                                                   20
```

METHOD FOR NUCLEIC ACID ANALYSIS USING FLUORESCENCE RESONANCE ENERGY TRANSFER

This application is a continuation of prior U.S. application Ser. No. 08/767,979 filed Dec. 17, 1996, now U.S. Pat. No. 5,945,283, which claims benefits of prior U.S. provisional application Ser. No. 60/008,743 filed Dec. 18, 1995, now abandoned.

REFERENCE TO GOVERNMENT GRANT

This invention was made with government support under Grant Numbers DE-FG06-94ER61909 and 1-F32-HG00156-01. The government has certain rights in this invention.

BACKGROUND OF THE INVENTION

(1) Field of the Invention

This invention relates generally to nucleic acid analysis and, more particularly, to methods for detecting nucleic acid target sites with fluorescence labeled oligonucleotides and to use of the methods in DNA genotyping.

(2) Description of the Related Art

Nucleic acid analysis has become increasingly important in a number of applications including the genotyping of individuals such as in the diagnosis of hereditary diseases, the detecting of infectious agents, tissue typing for histocompatability, the identifying of individuals in forensic and paternity testing and monitoring the genetic make up of plants and animals in agricultural breeding programs (see, for example, Alford and Caskey, *Cur Opin Biotech* 5:29–33, 1994 which is incorporated by reference).

One approach to nucleic acid analysis uses probes which are complementary to a nucleotide or nucleotides in the nucleic acid. These analyses are typically performed in conjunction with amplification of the DNA being tested by the polymerase chain reaction (Saiki et al., *Science* 239:487–491, 1988 which is incorporated by reference). Two variations of this approach are the Genetic bit analysis method and the oligonucleotide ligation assay.

The Genetic bit analysis method involves hybridization of an oligonucleotide to a DNA sequence immediately adjacent to a target nucleotide. The oligonucleotide then undergoes a 3' extension with a labeled dideoxynucleoside triphosphate and the labeled oligonucleotide is subsequently detected using enzyme linked colorimetry. (Nikiforov et al, *Nucleic Acids Res* 22:4167–4175, 1994 which is incorporated by reference).

The oligonucleotide ligation assay involves hybridization of a DNA sequence to two probes, one of which is labeled. One of the probes hybridizes to the nucleotides immediately contiguous to a target nucleotide and a second, allele-specific probe hybridizes to the target nucleotide and immediately contiguous nucleotides on the opposite side to the first probe. The two probes are then ligated and the resultant labeled oligonucleotide is detected using enzyme linked colorimetry (Nickerson et al., *Proc Natl Acad Sci* 87:8923–8927, 1990; U.S. Pat. Nos. 4,883,750, 4,988,617 and 5,242,794 all of which are incorporated by reference).

Both the genetic bit analysis and oligonucleotide ligation assay are time consuming and not readily adaptable to automation because they require capturing, separation, and washing of the labeled oligonucleotide followed by a multi-step detection procedure using an enzyme-linked immunosorbent assay.

In another approach, the detection of one or more nucleotides in a nucleic acid is accomplished using oligonucleotide probes labeled with two fluorescent substances in close proximity. One of the fluorophores (donor) has an emission spectrum that overlaps the excitation spectrum of the other fluorophore (acceptor) and transfer of energy takes place from the donor to the acceptor through fluorescence resonance energy transfer (T. Foster, Modern Quantum Chemistry, Istanbul Lectures, Part III, 93–137, 1965, Academic Press, New York which is incorporated by reference). The energy transfer is mediated by dipole-dipole interaction. Spectroscopically, when the donor is excited, its specific emission intensity decreases while the acceptor's specific emission intensity increases, resulting in fluorescence enhancement.

The fluorescence enhancement has been used in detection systems in which either two singly labeled oligonucleotides (Heller et al., EPO patent applications 0070685, 1983 which is incorporated by reference) or one doubly labeled oligonucleotide probe (Heller, EPO patent application 0229943, 1986 which is incorporated by reference) are first prepared and then hybridized to a target DNA or RNA sequence. The two fluorescent labels are separated by less than 22 nucleotides in the case of two singly labeled oligonucleotides or from 2 to 7 intervening base units in the case of doubly labeled oligonucleotide probes such that enhanced emission from fluorescent energy transfer can be detected from the hybridized probes.

The so-called Taqman assay uses a fluorescent energy transfer detection method which takes advantage of the decrease in emission intensity, i.e. or quenching observed in the first fluorophore. (Livak et al., *PCR Methods and Applications* 4:357–362, 1995; U.S. Pat. No. 5,528,848 which are incorporated by reference). An oligonucleotide containing the two fluorescent substances is hybridized to a target DNA sequence. The fluorescent substances are covalently linked to the oligonucleotide at a distance such that fluorescent energy transfer takes place which is then measured as a quenching of donor fluorescence. During amplification by polymerase chain reaction, the oligonucleotide is degraded thus separating the two fluorescent substances. As a result, the donor shows a loss of quenching and increase in fluorescent emission. Thus, by monitoring the loss of quenching of the donor, the target DNA sequence is detected.

One application of the TaqMan assay is in detecting single nucleotide polymorphisms, i.e. single base mutations in DNA. This method provides significant advantages over earlier assays for single nucleotide polymorphisms which were labor intensive and not readily automated. (see, for example, Botstein et al., *Am J Human Genetics* 32:314–331, 1980; Hayashi, *PCT Methods and Applications* 1:34–38, 1991; Meyers et al., *Methods in Enzymology* 155:501–527, 1987; Keen et al., *Trends in Genetics* 7:5, 1991; Cotton et al., *Proc Natl Acad Sci* 85:4397–4401; Myers et al., *Science* 230:1242–1246, 1985; and Kwok et al., *Genomics* 23:138–144, 1994 which are incorporated by reference). Nevertheless, a significant problem with the TaqMan assay results from a relative intolerance to mismatches which is disadvantageous for allelic discrimination. (Livak et al, *PCR Methods and Applications* 4:357–362, 1995 which is incorporated by reference). Thus, there remains a continuing need for an effective nucleic acid assay method that is simple to perform and readily automated.

SUMMARY OF THE INVENTION

Accordingly, therefore, the inventors herein have succeeded in discovering a new approach for detecting the presence of a target site of at least one nucleotide in a sample of nucleic acid using a fluorescent energy transfer detection method. The method involves synthesizing an oligonucleotide hybridized to a sequence of contiguous nucleotides, which include a target site of at least one nucleotide, in a nucleic acid. An essential feature of the oligonucleotide is that once formed, the oligonucleotide contains at least two fluorophores each of which is covalently bound to a separate nucleotide in the oligonucleotide. The two fluorophores are selected so that the emission spectrum of one fluorophore, referenced herein as the donor fluorophore, overlaps the excitation spectrum of the other, referenced herein as the acceptor fluorophore. The position of the two fluorophores on the oligonucleotide is such that upon release of the oligonucleotide from hybridization to the nucleic acid target site, the two fluorophores are separated by a distance that allows a fluorescence energy transfer to take place from the donor to the acceptor. The fluorescence energy transfer is then detected, either by decreased emission of the donor fluorophore or by an increase in emission of the acceptor fluorophore to indicate that the target site is present in the nucleic acid.

In one embodiment of the present invention, the oligonucleotide is formed by hybridizing a first polynucleotide which contains one of the two fluorophores to the nucleic acid. The hybridization is to a sequence of nucleotides in the nucleic acid that either includes or is immediately 3' to the target site. The second fluorophore is covalently linked to a dideoxynucleoside triphosphate which binds to the nucleic acid immediately 5' to the binding of the polynucleotide and is added by template directed synthesis to the 3' end of the polynucleotide at the target site. Fluorescence energy transfer from one fluorophore to the other is then detected upon denaturation and release of the oligonucleotide from the nucleic acid.

In another embodiment of the present invention the oligonucleotide is formed by hybridizing a first polynucleotide covalently linked to one fluorophore to the nucleic acid. A second polynucleotide covalently linked to the other fluorophore is hybridized to a sequence at contiguous nucleotides in the nucleic acid and immediately adjacent to the sequence of nucleotides hybridized to the first polynucleotide. The two polynucleotides are then covalently bonded together by template directed ligation to produce the oligonucleotide. Upon denaturation and release of the oligonucleotide from the nucleic acid, the fluorescent energy transfer from one fluorophore to the other is detected.

The present invention also provides for kit for detecting the presence of a target site of at least one nucleotide in a nucleic acid. The kit is comprised of (a) a polynucleotide covalently linked to one fluorophore and capable of binding to the target site or immediately 3' to the target site; and (b) a second other fluorophore covalently linked to a dideoxynucleoside triphosphate which is capable of binding to a target nucleotide in the nucleic acid at a position immediately 5' to the polynucleotide capable of adding by 3' extension to the polynucleotide. The emission spectrum of one of the fluorophores overlaps the excitation spectrum of the other.

Another embodiment of the present invention provides for a kit for detecting the presence of a target site of at least one nucleotide in a nucleic acid, the kit comprising (a) a first polynucleotide covalently linked to one fluorophore; and (b) a second polynucleotide covalently linked to a second fluorophore wherein the second polynucleotide is capable of being ligated to the first polynucleotide to form an oligomer which binds to the target site.

Among the several advantages found to be achieved by the present invention, therefore, may be noted the provision of new methods for detecting the presence of a specific nucleotide sequence in a nucleic acid; the provision of new methods for detecting nucleotide polymorphisms; the provision of methods that permit nucleic acid analysis that is inexpensive, simple, accurate, and adaptable to automation; the provision of methods that are adaptable for use in diagnosis of hereditary diseases and pathologic conditions, in the detecting of infectious agents, in tissue typing for histocompatability, in forensic identification and paternity testing and in monitoring the genetic make up of plant and animal.

BRIEF DESCRIPTION OF THE DRAWINGS

The file of this patent contains at least one drawing executed in color.

DESCRIPTION OF THE PREFERRED EMBODIMENTS

Figure 1:
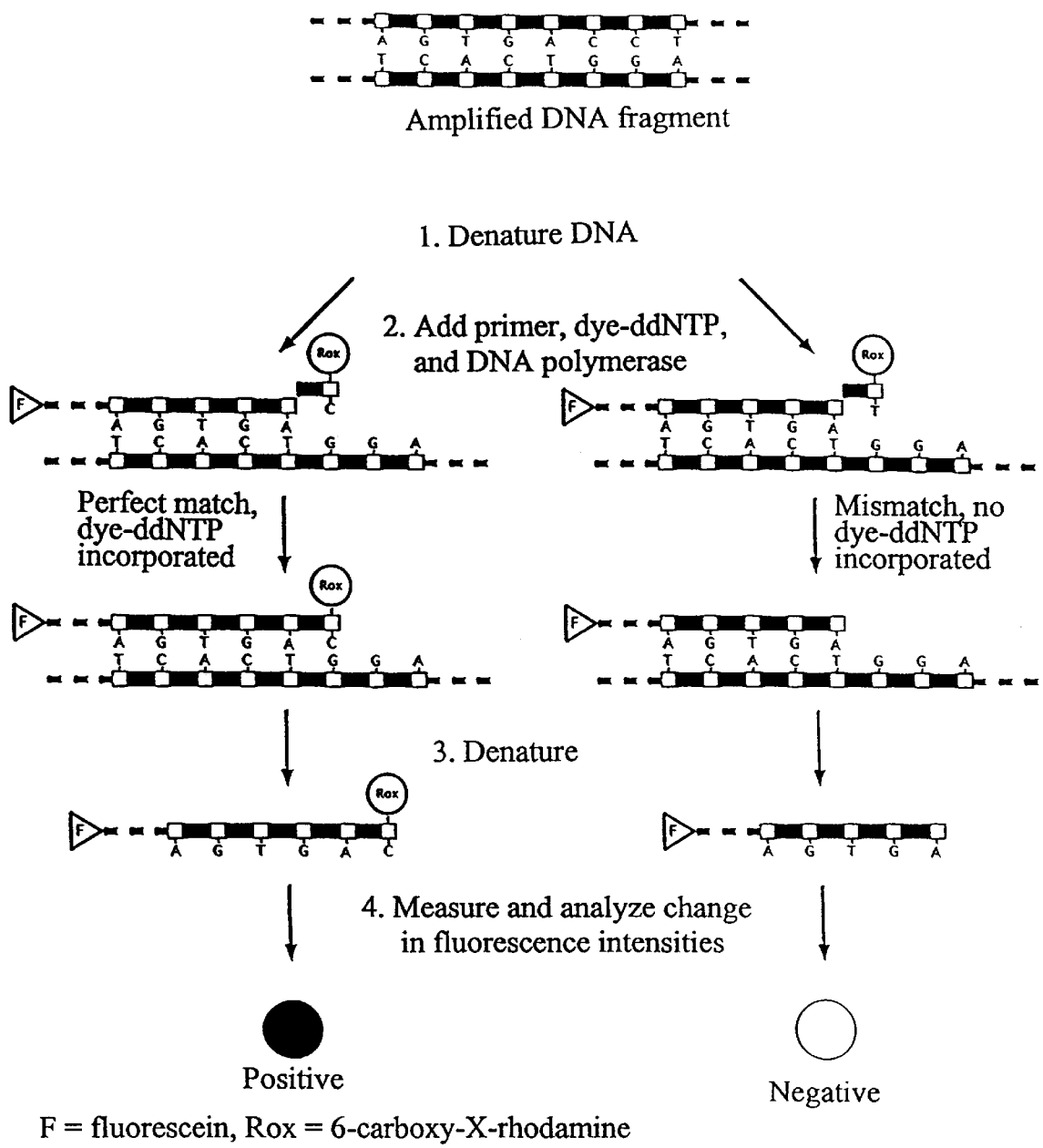
FIG. 1 illustrates the template directed nucleotide incorporation detection method.
Figure 2:
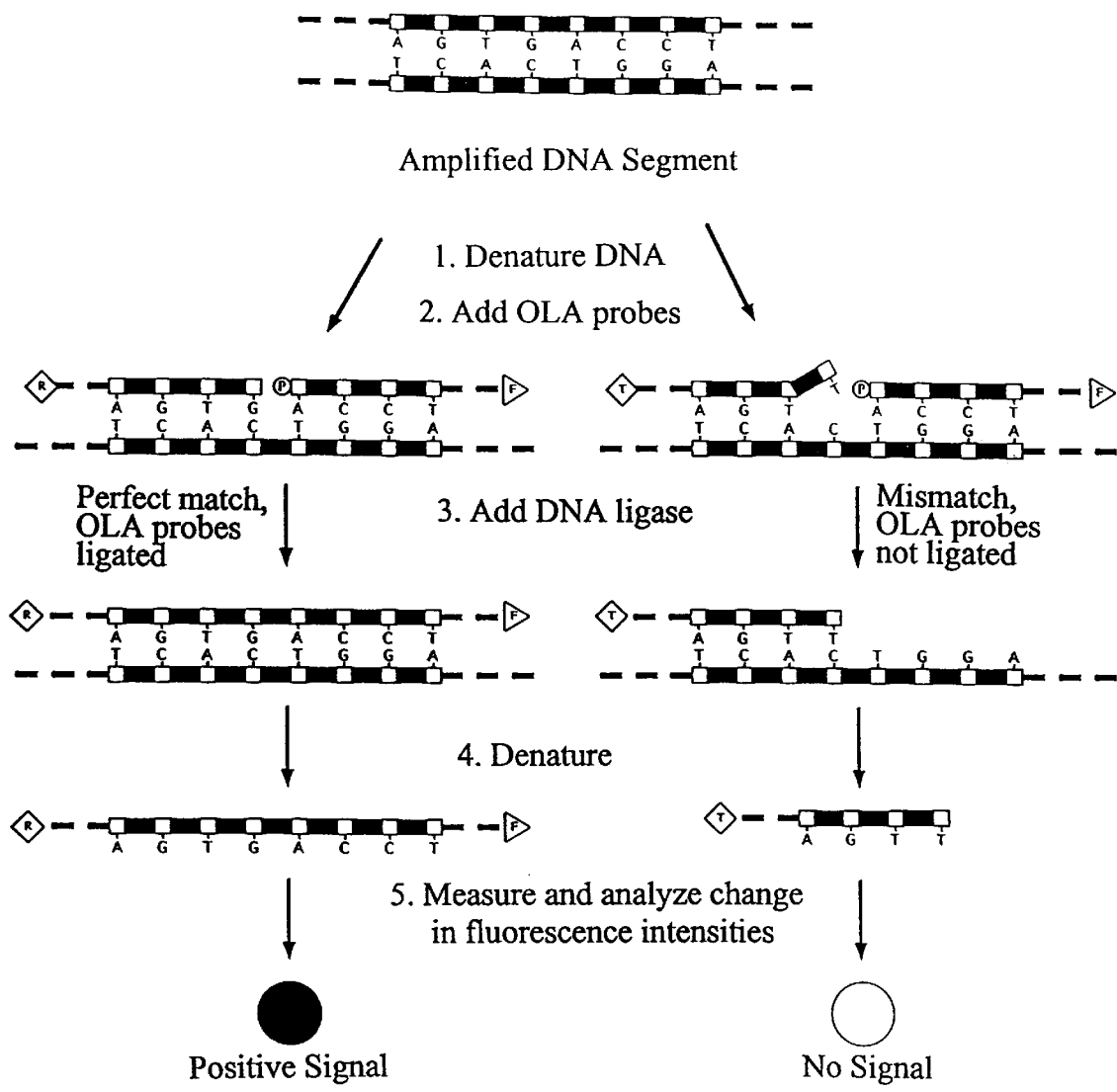
FIG. 2 illustrates the template directed polynucleotide ligation detection method.

The present invention is based upon the discovery that an oligonucleotide labeled with two fluorophores capable of showing a detectable fluorescence energy transfer can be constructed on a target nucleotide or nucleotide sequence in a nucleic acid so that the synthesized oligonucleotide becomes a probe hybridized to the nucleic acid. Surprisingly, the oligonucleotide can serve as an indicator of the presence of the target nucleotide or nucleotide sequence upon denaturation and release of the oligonucleotide from hybridization to the nucleic acid.

The doubly labeled oligonucleotide of the present invention is formed on the target nucleotide or nucleotide sequence of the nucleic acid from a singly labeled nucleotide or polynucleotide. Thus, upon formation of the doubly labeled oligonucleotide, fluorescence resonance energy transfer can be measured either as a quenching of the donor or increased emission of the acceptor.

Formation, i.e. synthesis, of the doubly labeled oligonucleotide on the target nucleic acid can be by any suitable method so long as the formation step requires the presence of the target nucleotide or nucleotides and a change in fluorescent energy transfer between the two fluorophores can be detected upon denaturation of the oligonucleotide. Preferably, in one embodiment a DNA or RNA polymerase enzyme and in another embodiment a DNA or RNA ligase enzyme is used to form the doubly labeled oligonucleotide on the target nucleic acid template.

One preferred method for preparation of the doubly labeled oligonucleotide hybridized to the target involves first providing a polynucleotide primer designed to hybridize to a target nucleic acid and labeled with one of two fluorophore substances (either a donor or acceptor) capable of fluorescence resonance energy transfer. In the case of genotyping assays where a single nucleotide polymorphism is being detected, the probe binds immediately 3' to the polymorphic site. Each of two dideoxynucleotides representing two possible alleles are labeled with the second fluorophore substance of the donor/acceptor pair. Two samples of target DNA are placed in separate reaction vessels and then to each sample is added a polynucleotide labeled with one member of the donor/acceptor fluorescent dye pair and one of the two dideoxynucleotides complementary to the alleles which is labeled with the other member of the dye pair. The two samples are then incubated under suitable conditions under which the polynucleotide hybridizes to the nucleic acid sample and in the presence of a thermostable DNA polymerase. The reaction is cycled between thermophilic and mesophilic temperatures under conditions such that the polynucleotide is extended by one base when the dideoxynucleoside triphosphate is complementary to the base on the target DNA responsible for the allele. Such conditions suitable for hybridization and for 3' addition of dideoxynucleoside triphosphates are known in the art (see for example, Sambrook et al., supra; Nikiforov et al, *Nuc Acids Res* 22:4167–4175, 1994; Yershov et al., *Proc Natl Acad Sci* 93:4913–1918, 1996 which are incorporated by reference). The hybridized primer is only extended when the added dideoxynucleotide is complementary to the target DNA at the polymorphic site. After denaturing to release the doubly labeled oligonucleotide from hybridization to the target, the reaction mixture can be analyzed in a fluorescence spectrophotometer. Fluorescence energy transfer occurs in the single strand, doubly labeled oligonucleotide when a labeled dideoxynucleotide has been incorporated into the hybridized polynucleotide probe. Alternatively, instead of identifying the different alleles in separate incubation reactions, the dideoxynucleoside triphosphates can contain different and distinguishable acceptor or donor fluorescent dyes in which the excitation or emission spectrum differs. This allows the detection of both alleles in the same reaction vessel by detecting a different donor/acceptor reaction for each allele. At least from two to four or more individual acceptor fluorophore-labeled dideoxynucleoside triphosphates can be used in a single reaction so long as the enhanced emission spectra from the acceptor fluorophores are distinguishable. A significant advantage of this method allows for the sequential amplification of a target template nucleotide, the degradation of excess deoxy nucleoside triphosphates and single stranded polynucleotides, and the detection of a target nucleotide sequence to be accomplished in one reaction vessel without the requirement for separation or purification steps.

In a second embodiment, the doubly labeled oligonucleotide is formed by ligation of two singly labeled polynucleotides, each polynucleotide having a sequence complementary to the target nucleic acid. In the case of genotyping assays where a single nucleotide polymorphism is being detected, a first of the two labeled polynucleotides contains a nucleotide complementary to one of two possible nucleotides at the allelic site at either its 3' or 5' end and is otherwise complementary to nucleotides in the nucleic acid that are contiguous with the allelic site. Two such labeled polynucleotides are prepared, one for each allele with one of two different and distinguishable acceptors covalently linked to the allele specific polynucleotide. The second of the two labeled polynucleotides is complementary to the nucleotides that are contiguous to and positioned in the nucleic acid sequence on the other side of the allelic site. The other of the two donor/acceptor fluorescent dye substances is covalently linked to the second polynucleotide. In two parallel reactions, the target DNA sample is incubated with one of the first allele-specific, labeled polynucleotide probes along with the second labeled polynucleotide probe in the presence of a thermostable ligase followed by cycling between thermophilic and mesophilic temperatures. If the acceptor dye-labeled, allele-specific probe perfectly complements the target DNA, it is ligated to the donor dye-labeled probe. After stopping the reaction and denaturing to release the formed, doubly labeled oligonucleotide from hybridization to the nucleic acid, fluorescence is analyzed in a fluorescence spectrophotometer. Alternatively, instead of identifying the different alleles in separate incubation reactions, the allele-specific, first labeled polynucleotides can contain different acceptor or donor fluorescent dyes in which the excitation or emission spectrum is distinguishably different. As with the single nucleotide addition above, this approach allows the detection of two or more alleles in the same reaction vessel by detecting a different donor/acceptor reaction for each allele.

As described earlier, the oligonucleotide is released from the nucleic acid for measurement of fluorescence energy transfer from donor to acceptor. In certain variations of this embodiment, however, the doubly labeled oligonucleotide need not be free in solution, but can be anchored to a support to facilitate automation. Furthermore, the present invention is applicable to DNA chip technology such that a particular marker polynucleotide is at a particular address site on the chip (Pease et al., *Proc. Natl. Acad. Sci.* 91:5022–6, 1994 which is incorporated by reference).

Fluorescent dye-labeled dideoxynucleoside triphosphates and polynucleotide probes can be purchased from commercial sources. Labeled polynucleotides probes can also be prepared by any of a number of approaches. For example, unlabeled polynucleotides can be prepared by excision, transcription or chemical synthesis. Labeling of the polynucleotide probe with a fluorescent dye can be done internally or by end labeling using methods well known in the art (see, for example, Ju et al., *Proc Nat Acad Sci* 92:4347–4351, 1995; Nelson et al. *Nucleic Acids Res* 20:6253–6259, 1992 which are incorporated by reference).

The oligonucleotides and polynucleotides of the present invention are able to form a hybrid structure with a nucleic acid sequence containing the specific target nucleotide or nucleotide sequence, due to complementarity with the target or to a portion of the nucleic acid sequence containing the target. Oligomers suitable for hybridizing to the nucleic acid contain a minimum of about 6–12 contiguous nucleotides which are substantially complementary to the nucleic acid, and preferably about 15 to about 60 nucleotides in length; more preferably from about 18 to about 40 nucleotides in length; and still more preferably from about 20 to about nucleotides in length. Where the fluorophores are not positioned at the 5' and 3' ends of the synthesized oligonucleotides but, instead, are placed internally, the oligonucleotides and polynucleotides from which they are made can be substantially longer: preferably from about 18 to about 1000; preferably from about 20 to about 200 or more nucleotides, more preferably from about 30 to about 100 nucleotides and more preferably from about 40 to about 80 nucleotides.

The oligonucleotide or polynucleotide includes linear oligomers of natural or modified monomers including deoxyribonucleotides, ribonucleotides and the like, capable of specifically binding to a target polynucleotide by way of monomer to monomer interactions such as through Watson-Crick type base pairing.

Specific hybridization or specific binding with respect to a polynucleotide to a complementary polynucleotide as used herein is intended to mean the formation of hybrids between a polynucleotide and a particular target polynucleotide sequence wherein the polynucleotide preferentially hybridizes to the target polynucleotide sequence over sequences other than the target polynucleotide. The polynucleotide or oligonucleotide can be perfectly matched such that the strands making up the duplex form a double stranded structure with one another and every nucleotide in each strand undergoes Watson-Crick base pairing with a nucleotide in the other strand. A mismatch in a duplex between a target polynucleotide and an oligonucleotide or polynucleotide means that a pair of nucleotides in the duplex fails to undergo Watson-Crick bonding.

The stringency of hybridization is determined by a number of factors during hybridization and during the washing procedure including temperature, ionic strength, length of time and concentration of formamide. These factors are outlined in, for example, Sambrook et al. (Sambrook et al., *Molecular Cloning: A Laboratory Manual* 2nd Ed., 1989 Cold Spring Harbor Laboratory Press, Cold Spring Harbor, N.Y. which is incorporated by reference).

The present invention uses fluorescence resonance energy transfer between two fluorophores each covalently linked to a separate nucleotide in the detection of a specific nucleotide or nucleotide sequence in a sample of nucleic acid. The emission spectrum of one of the two fluorophores, the donor, overlaps the excitation spectrum of the other, the acceptor. As a result, when the donor is excited its emission is diminished or quenched due to resonance transfer of energy to the acceptor fluorophore and the emission of the acceptor fluorophore is enhanced.

Any of a number of fluorophore combinations can be selected for use in the present invention (see for example, Pesce et al,. eds, *Fluorescence Spectroscopy*, Marcel Dekker, New York, 1971; White et al., *Fluorescence Analysis*: A practical Approach, Marcel Dekker, New York, 1970; *Handbook of Fluorescent Probes and Research Chemicals*, 6th Ed, Molecular Probes, Inc., Eugene, Oreg., 1996; which are incorporated by reference). In general, a preferred donor fluorophore is selected that has a substantial spectrum of the acceptor fluorophore. Furthermore, in may also be desirable in certain applications that the donor have an excitation maximum near a laser frequency such as Helium-Cadmium 442 nM or Argon 488 nM. In such applications the use of intense laser light can serve as an effective means to excite the donor fluorophore. The acceptor fluorophore has a substantial overlap of its excitation spectrum with the emission spectrum of the donor fluorophore. In addition, the wavelength maximum of the emission spectrum of the acceptor moiety is preferably at least 10 nm greater than the wavelength maximum of the excitation spectrum of the donor moiety. The emission spectrum of the acceptor fluorophore is typically in the red portion of the visible spectrum, although, it is believed that acceptor fluorophores having emission at longer wavelengths in the infrared region of the spectrum can be used. A list of examples of fluorophore donor/acceptor combinations is shown in Table 1. The combinations shown are intended to be exemplary only and are not intended to be construed as a limitation of the present invention.

TABLE 1

| Donor | Acceptor |
|---|---|
| Fluorescein | ROX[1] |
| | TAMRA[2] |
| | Rhodamine |
| | Texas Red |
| | Eosin |
| Cascade Blue | Fluorescein |

TABLE 1-continued

| Donor | Acceptor |
|---|---|
| BODIPY ® 530/550[3] | BODIPY ® 542/563[4] |
| BODIPY ® 542/563[4] | BODIPY ® 564/570[5] |

[1]6-carboxy-X-rhodamine (Applied Biosystems Division of Perkin-Elmer Corporation, Foster City, CA).
[2]N,N,N', N'-tetramethyl-6-carboxy-rhodamine (Applied Biosystems Division of Perkin-Elmer Corporation, Foster City, CA), herein tetramethyl-6-carboxy-rhodamine.
[3]BODIPY ® is a registered trademark (Molecular Probes, Eugene, Oregon) used for the fluorophore 4,4-difluoro-5,7-diphenyl-4-bora-3a,4a-diaza-S-indacene. The numbers following the name (BODIPY ®) reflect the excitation and emission maxima of derivatives or the parent compound.
[4]BODIPY ® is a registered trademark (Molecular Probes, Eugene, Oregon) used for the fluorophore 4,4-difluoro-5-p-methoxyphenyl-4-bora-3a,4a-diaza-S-indacene.
[5]BODIPY ® is a registered trademark (Molecular Probes, Eugene, Oregon) used for the fluorophore 4,4-difluoro-5-styryl-4-bora-3a,4a-diaza-S-indacene.

Fluorescence resonance energy transfer from a donor to an acceptor fluorophore is known to be dependent upon the distance between the fluorophores. In one study, the transfer efficiency was shown to decrease from a value close to 100% for separation distances of about 12 Angstroms (equivalent to about 3.5 nucleotides) to 16% for a separation distance of about 45 Angstroms (equivalent to about 13 nucleotides). Heller et al. (EP application 0229943) reported that when attached to individual nucleotides of a polynucleotide by 14 Angstrom linker arms, the highest efficiency of energy transfer amounting to 82% occurs at a separation of 5 nucleotide base units when hybridized to the target DNA although a range of 2 to 7 intervening base pairs is taught in this reference. In the unhybridized state, the maximum efficiency was 50% at a separation of 9 nucleotide base units. At a distance of 12 nucleotides separation, the efficiency dropped to 12%.

In contrast, in the present study, separations of the donor and acceptor fluorophores by about 20 nucleotides and about 40 nucleotides produced detectable fluorescence resonance energy transfer. It is noted, however, that in the earlier work reported by Heller et al. the linker arms could also produce an additional separation of fluorophores which could be comparable to longer nucleotide sequences for a given percent efficiency. Nevertheless, although not intending to be bound by any theory, it is possible that fluorescence resonance energy transfer is achieved in the present invention as a result of a hydrophobic interaction between the organic dye molecules when the doubly labeled oligonucleotide is free and in solution. Because the oligonucleotide conformation is no longer restricted by hybridization to the nucleic acid, hydrophobic interaction of the two dyes could result in the donor/acceptor pair of fluorophores being in close proximity to one another even when placed on the oligonucleotide as much as 20 to 40 base pairs apart. Such extreme separation would not have been predicted to allow fluorescence resonance energy transfer based upon the earlier data obtained using probes hybridized to the target nucleic acid.

A significant disadvantage of earlier approaches arose from the requirement that the fluorescent dyes be in close proximity. As a result, in order to hybridize to the target sequence it was necessary to internally label longer oligonucleotide probes. Because the present method measures fluorescence resonance energy transfer upon denaturation and release from hybridization to the target nucleic acid, the oligonucleotide of the present invention can be end labeled with each of the donor/acceptor fluorophores.

Thus, in the present invention the preferred distances between fluorophores is determined not only by the fluorescence resonance energy transfer but, also by the polynucleotide lengths required for hybridization. Because the hybridization is crucial to the assay method, the polynucleotide and oligonucleotide lengths suitable for hybridization are generally believed to be more important so long as a detectable fluorescence resonance energy transfer can be detected. Thus, because the polynucleotide probes must first hybridize to the target nucleic acid for the dideoxynucleoside triphosphate method, doubly labeled oligonucleotides with a fluorophore separation of about 20 nucleotides is preferred. With the ligation method, however, oligonucleotides with a fluorophore separation of about 40 oligonucleotides is preferred because each of two 20-mer polynucleotides that form the oligonucleotide are each required to hybridize to the targeted nucleic acid.

The nucleic acid sample for testing according to the methods in this invention can be obtained from virtually any source including virus, bacteria, fungi, plants, invertebrates and vertebrates including humans and other mammals, birds and the like. If only small amounts of a particular target nucleic acid are available in the sample, amplification by polymerase chain reaction can be used in preparation for analysis (see, for example, Kwok et al., *Genomics* 23:138–144, 1994 which is incorporated by reference).

Four species are monitored at the end of the assay for three types of fluorescence emission. Two species are the free donor ($D_f$) and acceptor ($A_f$) dye ligands; the others are the donor and acceptor dye ligands ($D_b$ and $A_b$) covalently linked to the oligonucleotide. Total acceptor emission ($A_f + A_b$) is determined by exciting the reaction mixture at the acceptor's excitation maximum wavelength and measuring emission at its emission maximum. Exciting the reaction mixture at the donor ligand's excitation maximum and measuring emitted light at the donor's emission maximum gives ($D_f + D_b$) fluorescence due to free donor ligands and quenched fluorescence due to the donor ligands covalently linked to the oligonucleotide. Enhanced acceptor emission ($A_e$) is determined by exciting at the donor ligand's excitation maximum and measuring emitted light at the acceptor ligand's emission maximum. ($A_e/[A_f + A_b]$) normalizes the acceptor fluorescence to account for variations in acceptor dye ligand concentrations between reactions.

Typically assays include appropriate controls that are commonly used in the art. For example, two DNA samples known to contain one allele and two DNA samples known to contain the second allele can be used. These can serve as positive and negative controls for the alleles assayed. A random PCR product without the allelic site can also serve as a negative control.

Fluorescence enhancement (FE) is measured from the formula $FE = [A_e/(A_f + A_b)]/(D_f + D_b)$. Results are positive when $FE_{sample} > [FE_{control} + 6.95 \times \text{Standard Deviation}_{control}]$ which is equivalent to statistical significance at the 99% confidence level in the Students t-Test.

Unlike the prior art, the present invention does not require radioactive reagents, product capture, product separation, or multi-step post-reaction processing and purification. The invention is highly suitable for processing large numbers of DNA samples in parallel, is easier to use than those in the prior art, and can be automated.

Kits are packaged to aid research, clinical, and testing labs to carry out the invention. For the dideoxynucleoside triphosphate based assays, kits contain an oligonucleotide that binds immediately 3'- to a polymorphic site labeled with one member of a donor/acceptor fluorescent dye pair and each of two or more dideoxynucleoside triphosphates complementary to the alleles labeled with different fluorophores constituting the other member of the dye pair, and may include thermostable DNA polymerase, other buffers and reagents needed for the procedure, and instructions for carrying out the assay.

For oligonucleotide ligation assays, kits contain two polynucleotides, each having a sequence complementary to the target DNA that includes an allelic site, and each is labeled with one of two or more different fluorescent acceptors dyes having different emission maxima, and an polynucleotide having a sequence complementary to the target DNA at a site immediately adjacent to the allelic site labeled with a donor fluorescent dye chosen so that its emission spectrum overlaps the excitation spectrum of both acceptor dyes. Oligonucleotide ligation assay kits may also include a thermostable ligase, other buffers and reagents needed for the procedure, and instructions for carrying out the assay.

The kits contain a single set of polynucleotide and/or dideoxynucleoside triphosphate reagents to detect a single allelic difference or sets of reagents to detect multiple alleles. Kits can be packaged for manual or automated procedures. All reagents are packaged in containers for storage at either freezer, refrigerator, or room temperature.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates the identification of a single base difference between four unique synthetic forty mer nucleic acid molecules using a template directed nucleotide incorporation assay.

Synthetic polynucleotides were used to establish the sensitivity and specificity of fluorescence resonance energy transfer in detecting fluorophore labeled dideoxynucleoside incorporation. A set of four 40 mers comprised of an identical sequence except for the base at position twenty-one were synthesized. Each of the four possible bases A, C, G or T were uniquely represented at position 21 in each of the four different templates as shown in Table 2. The fluorescein-labeled polynucleotide was synthesized and purified by reverse-phase HPLC by the supplier (GENSET Corp., La Jolla, Calif.). The template 40 mers were synthesized by the Genome Sequencing Center at Washington University (St. Louis, Mo.).

TABLE 2

| Oligomer | Nucleotide Sequence[2] | SEQ ID NO: |
|---|---|---|
| s14102-40A | 5'-ATTTTACAAAAATAAAACAA<u>A</u>GAAACCACTAAGCCATAAA | 1 |
| s14102-40C | 5'-ATTTTACAAAAATAAAACAA<u>C</u>GAAACCACTAAGCCATAAA | 2 |
| s14102-40G | 5'-ATTTTACAAAAATAAAACAA<u>G</u>GAAACCACTAAGCCATAAA | 3 |
| s14102-40T | 5'-ATTTTACAAAAATAAAACAA<u>T</u>GAAACCACTAAGCCATAAA | 4 |
| s14102-F[1] | 5'-F[1]-TTTATGGCTTAGTGGTTTC | 5 |

[1]Fluorescein label.
[2]Underlined nucleotides are unique to that sequence.

Each 40 mer served as a template in four separate reactions where it was incubated with the 5' fluorescein-labeled polynucleotide and one of four 6-carboxy-X-rhodamine conjugated dideoxynucleoside triphosphates in the presence of Klentaq1-FY (obtained from the laboratories of Dr. Wayne Barnes, Washington University, St. Louis, Mo.) and the other three non-labeled dideoxynucleoside terminators. 6-carboxy-X-rhodamine conjugated dideoxynucleoside triphosphates were obtained from DuPont NEN (Boston, Mass.). Non-labeled dideoxynucleoside triphosphates were purchased from Pharmacia Biotech (Piscataway, N.J.). Reactions were performed in 20 $\mu$l reaction volumes containing 50 mM Tris-HCl, pH 9.0, 50 mM KCl, 5 mM NaCl, 5 mM $MgCl_2$, 8% glycerol, 0.1% Triton X-100, 25 nM fluorescein-labeled primer, 100 nM 6-carboxy-X-rhodamine conjugated dideoxynucleoside triphosphate, >50 nM of a synthetic 40-mer, and 250 nM of the other three non-labeled dideoxynucleoside triphosphates. Reactions were incubated in a GeneAmp 9600 thermo cycler (Perkin/Elmer) at 93° C. for one minute, and followed by thirty five cycles of 93° C. for ten seconds and 50° C. for thirty seconds. Reactions were terminated by the addition of 10 $\mu$L of 50 mM EDTA, pH 9.0.

At the end of the reaction, products may be analyzed by at least one of three independent methods. One method resolves products and reactants in a sequencing gel (6% polyacrylamide, 8M urea, 1×Tris Borate EDTA buffer) on an Applied Biosystems 373A automatic DNA sequencer (Perkin/Elmer Applied Biosystems Division, Foster City, Calif.). Fluorescent species are analyzed using GeneScan 672 software (Perkin/Elmer) to monitor the incorporation of fluorophore-labeled dideoxynucleoside triphosphates. Another method involves denaturing and diluting the reaction mixtures with the addition of 150 $\mu$l 0.2N NaOH. The diluted reaction mixtures are transferred to a 96-well white microplate (Perkin/Elmer). The fluorescence emission of the fluorophores is determined using a Luminescence Spectrometer LS-50B (Perkin/Elmer). A preferred method measures the fluorescence intensity changes during thermal cycling using the Sequence Detection System 7700 (Perkin/Elmer) without any further manipulations or reaction sampling.

Figure 3:
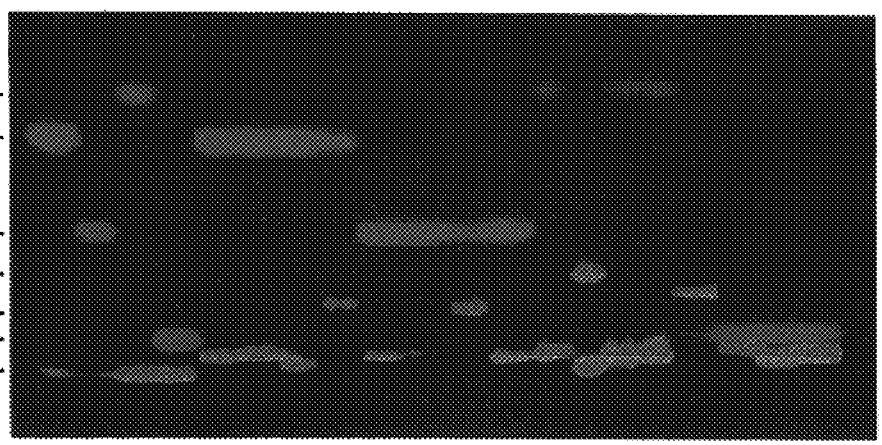
FIG. 3 illustrates a GeneScan gel image of template directed nucleotide incorporation assay samples separated on a 6% sequencing gel showing the positions of donor fluorophore-labeled primer, acceptor fluorophore-labeled dideoxynucleotide triphosphate, donor/acceptor fluorophore dual labeled primer, and the fluorescence intensities measured for each.
Figure 4:
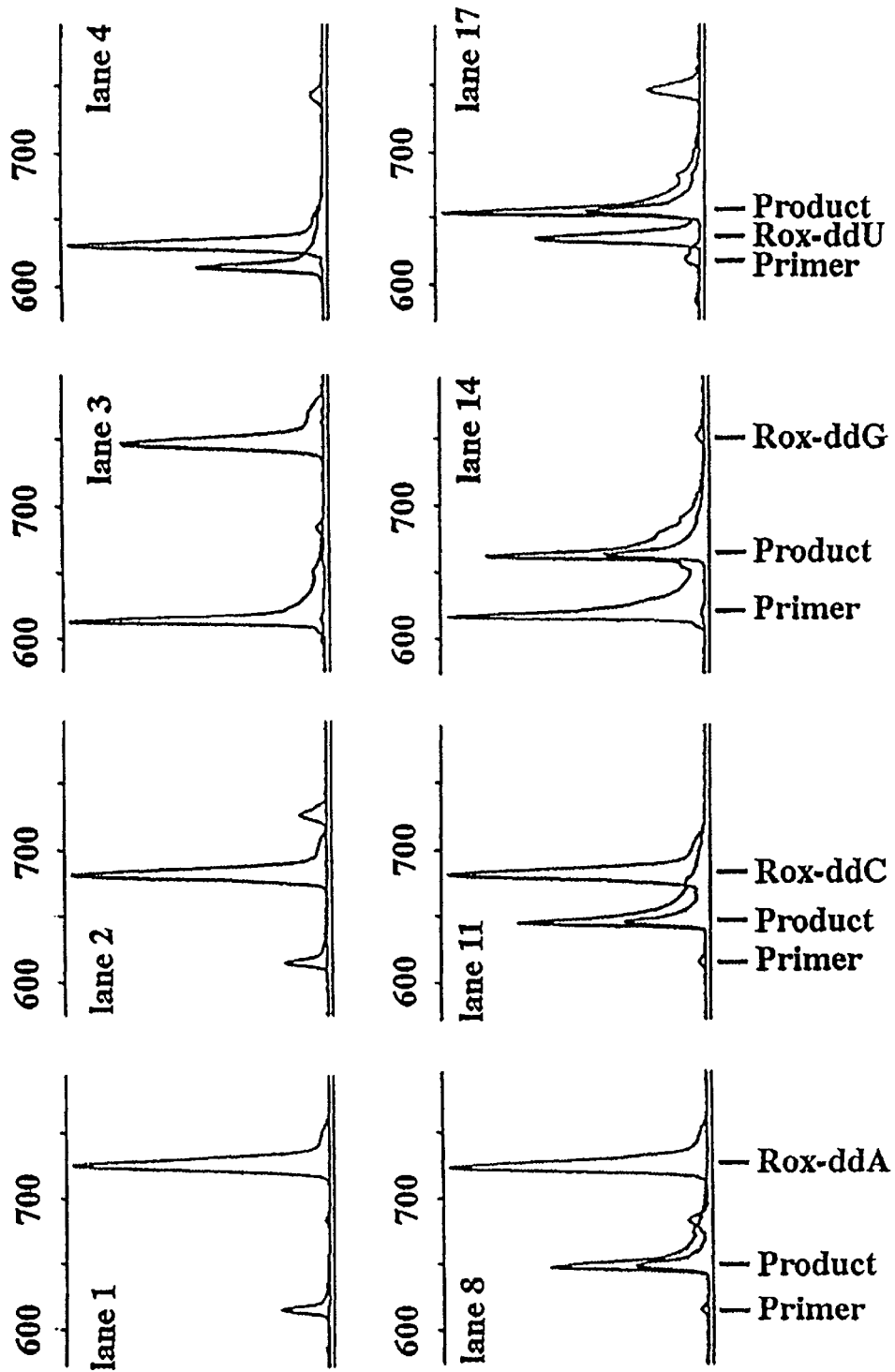
FIG. 4 illustrates a chromatogram of the fluorescence intensities observed in negative controls in lanes 1 through 4, and in positive samples in lanes 8, 11, 14 and 17 in FIG. 3.

The reactions above were analyzed after electrophoresis on a sequencing gel using the GeneScan analysis software. 2 µl of each reaction mixture was added to 3 µL of loading buffer (98% formamide and 10 mM EDTA) and loaded onto a sequencing gel and reactants and products were resolved by electrophoresis for 1.5 hours at 300V constant. Fluorescent species were analyzed using GeneScan 672 software to monitor the incorporation of fluorophore-labeled dideoxynucleoside triphosphates. The GeneScan gel image confirmed that only the one base that was perfectly complementary to the specific template was incorporated in each reaction (FIG. 3). Fluorescein labeled polynucleotides migrate slightly differently depending on the terminator incorporated. For example, the fluorescein signals for lanes 12, 16, and 20, in which non-labeled dideoxyadenosine was incorporated, migrated the same distance in the gel. The same was observed for the signals in lanes 7, 15, and 19 for dideoxycytosine incorporation, lanes 6, 10, and 18 for dideoxyguanidine incorporation, and lanes 5, 9, and 13 for dideoxyuridine incorporation. In lanes in which a 6-carboxy-X-rhodamine conjugated dideoxynucleoside was incorporated, the fluorescein and 6-carboxy-X-rhodamine signals comigrated and were retarded due to the fluorophore molecule as noted in lanes 8, 11, 14 and 17. Chromatograms of the control lanes (1–4) and the positive reaction lanes (8, 11, 14, 17) were produced (FIG. 4). The emission signals from fluorescein and from 6-carboxy-X-rhodamine are seen as separate peaks in the control lanes. However, the dual labeled oligonucleotide appears as a new peak, indicated as a comigrating fluorescein and 6-carboxy-X-rhodamine emission peak in the positive reaction samples, confirming the specificity of each reaction.

Fluorescence spectrophotometric analysis as shown in FIG. 3 of the reaction mixture at the end of the TDI assay showed that 3 types of changes in fluorescence intensity were observed when dye-terminators were incorporated. The first two types of changes were seen when the reaction mixture was excited by light at the fluorescein-specific absorption wavelength (488 nm), namely, a reduction in fluorescein-specific emission (FF) due to quenching by the incorporated dye and an increase in 6-carboxy-X-rhodamine-specific emission (FR) due to fluorescence resonance energy transfer. The third type of change was observed when the mixture was excited by light at the 6-carboxy-X-rhodamine-specific absorption wavelength (580 nm): a reduction in acceptor 6-carboxy-X-rhodamine (RR) emission due to quenching by the DNA oligomer to which the acceptor had attached. The fluorescence readings for each lane in FIG. 3 show these changes and in each of the 3 intensity changes, the difference between the positive reactions and negative reactions was highly significant, with the exception of the RR reading for 6-carboxy-X-rhodamine conjugated dideoxyguanidine. The $FE_s/FE_c$ ratios for the positive assays ranged from 190% to 360%.

Based on a series of dilution experiments using the single-stranded synthetic templates, significant differences were found between positive and negative reactions at >5 nM template concentrations (data not shown).

EXAMPLE 2

This example illustrates the identification of single nucleotide polymorphisms in human PCR amplified sequence tagged sites using a template directed nucleotide incorporation assay.

The most common DNA sequence variations are represented by single base pair mutations known as single nucleotide polymorphism. Approximately one polymorphic site is found for every 500 to 1,500 base pairs in human genomic DNA (D. N. Cooper et al., *Human Genetics*, 69:201–205, 1985). A significant fraction of these polymorphisms are known to be linked to genetic diseases. The template directed nucleotide incorporation assay provides a unique method for detecting the presence of a single nucleotide polymorphism in a nucleotide sample. Two human polymorphic sequence tagged sites, D18S8 (Parry et al., *Nucl. Acids Res.*, 19:6983, 1991, incorporated herein by reference), and DXS17 (Kornreich et al., Genomics, 13:70–74, 1992, incorporated herein by reference), each previously shown to contain a single nucleotide polymorphism, were used to show the sensitivity and specificity of the template directed nucleotide incorporation assay in typing these polymorphic alleles.

Polynucleotides for PCR amplification of these two independent sequence tagged sites, and sequence tagged site specific 5' end fluorescein-labeled polynucleotide probes were synthesized as in example 1. The DNA sequence of each sequence tagged site flanking the allelic marker, and the polynucleotides used to generate and identify those sequences are shown in Table 3. Forty independent human DNA sources with known genotypes were PCR amplified for each sequence tagged site. Target nucleic acid sequences were amplified in 200 µl thin walled polyallomer MicroAmp tubes (Perkin/Elmer) on a GeneAmp 9600 thermo cycler (Perkin/Elmer). AmpliTaq DNA polymerase was purchased from Perkin/Elmer Corporation (Foster City, Calif.). Fluorophore-labeled dideoxynucleoside triphosphates were obtained from DuPont NEN (Boston, Mass.). Unlabeled dideoxynucleoside triphosphates were purchased from Pharmacia Biotech (Piscataway, N.J.). Human genomic DNA (20 ng) from test subjects was amplified in 40 µl in 50 mM Tris HCl, pH 9.0, 50 mM KCl, 5 mM NaCl, 1.5 mM $MgCl_2$, 0.2 mM dNTP, 1 µM of each PCR primer, and AmpliTaq DNA polymerase (2U). PCR reaction mixtures were held at 94° C. for three minutes, followed by ten cycles of 94° C. for ten seconds, ramping to 68° C. over ninety seconds, held at 68° C. for thirty seconds, then followed by thirty cycles of 94° C. for ten seconds, and 62° C. for thirty seconds. The PCR products expected are a 367 base pair D18S8 segment, and a 620 base pair DXS17 segment. The PCR products were gel purified on a 1% agarose gel in 1×TAE buffer, stained with ethidium bromide, excised under long wavelength UV transillumination (365 nm), and extracted using the Promega Wizard PCR purification system (Promega Inc., Madison, Wis.).

The gel purified PCR reaction products were used as templates and subjected to template directed nucleotide incorporation analysis using appropriate fluorescein-labeled polynucleotides DXS17-F (SEQ ID:15) or D18S8-F (SEQ ID:10) as in Table 3. The templates were placed in two parallel reactions containing an appropriate fluorescein-labeled primer and one of the allelic 6-carboxy-X-rhodamine conjugated dideoxynucleoside triphosphates. Reactions were performed as in example 1, except that 25 nM fluorescein-labeled polynucleotide, 100 nM 6-carboxy-X-rhodamine conjugated dideoxynucleoside triphosphate, and >50 ng gel purified PCR reaction product were used. Samples of the reactions were analyzed by fluorescence spectroscopy, and the results are presented in Table 4 for DXS17 and in Table 5 for D18S8.

TABLE 3

| Oligomer | Sequence | SEQ ID NO: |
|---|---|---|
| D18S8-p1 | 5'-TTGCACCATGCTGAAGATTGT | 6 |
| D18S8-p2 | 5'-ACCCTCCCCCTGATGACTTA | 7 |
| D18S8 Allele A | 5'-AGGAGAATTGCTTGAACCCAGGAGGCAGAGCTTGCAGTGA | 8 |
| D18S8 Allele G | 5'-AGGAGAATTGCTTGAACCCGGGAGGCAGAGCTTGCAGTGA | 9 |
| D18S8 Probe | 5'-F[1]-CACTGCAAGTCTGCCTCC | 10 |
| DXS17-p1 | 5'-GCAATTATCTGTATTACTTGAAT | 11 |
| DXS17-p2 | 5'-GGTACATGACAATCTCCCAATAT | 12 |
| DXS17 Allele A | 5'-ATTGGATTATTTGTAAACTCAAAGGATAAGTGCATAAAGGG | 13 |
| DXS17 Allele G | 5'-ATTGGATTATTTGTAAACTCGAAGGATAAGT GCATAAAGGG | 14 |
| DXS17 Probe | 5'-F[1]-CCCTTATGCACTTATCCTT | 15 |

[1]Fluorescein

Fluorescence enhancement (FE) was calculated by the formula $FE=[A_e/(A_f+A_b)]/(D_f+D_b)$. PCR products that do not contain the specific alleles served as controls. Samples were scored positive when $FE_{sample} > [FE_{control} + 6.95 \times \text{Standard Deviation}_{control}]$. This corresponds to a cutoff ratio for $FE_{sample}/FE_{control}$ of 1.25. FF, FR, and RR values were obtained as in Example 1.

TABLE 4

TDI assay data for diallelic marker DXS17

| | Rox-ddC | | | | Rox-ddU | | | | |
|---|---|---|---|---|---|---|---|---|---|
| Sample | FF | FR/RR | FE | $FE_s/FE_c$ | FF | FR/RR | FE | $FE_s/FE_c$ | Genotype |
| 1 | 239 | 0.17 | 0.07 | 0.84 | 178 | 0.35 | 0.20 | 1.84 | T/T |
| 2 | 160 | 0.32 | 0.20 | 2.29 | 172 | 0.31 | 0.18 | 1.68 | C/T |
| 3 | 143 | 0.37 | 0.26 | 3.02 | 203 | 0.20 | 0.10 | 0.90 | C/C |
| 4 | 208 | 0.19 | 0.09 | 1.05 | 136 | 0.44 | 0.32 | 3.00 | T/T |
| 5 | 174 | 0.28 | 0.16 | 1.84 | 203 | 0.19 | 0.10 | 0.89 | C/C |
| 6 | 220 | 0.18 | 0.08 | 0.95 | 134 | 0.47 | 0.35 | 3.26 | T/T |
| 7 | 214 | 0.18 | 0.08 | 0.98 | 133 | 0.43 | 0.33 | 3.05 | T/T |
| 8 | 150 | 0.39 | 0.26 | 3.00 | 149 | 0.40 | 0.27 | 2.52 | C/T |
| 9 | 132 | 0.42 | 0.32 | 3.66 | 199 | 0.20 | 0.10 | 0.93 | C/C |
| 10 | 214 | 0.18 | 0.08 | 0.98 | 138 | 0.42 | 0.31 | 2.89 | T/T |
| 11 | 214 | 0.18 | 0.08 | 0.97 | 127 | 0.48 | 0.38 | 3.54 | T/T |
| 12 | 213 | 0.18 | 0.09 | 0.99 | 132 | 0.44 | 0.33 | 3.11 | T/T |
| 13 | 208 | 0.19 | 0.09 | 1.04 | 145 | 0.36 | 0.25 | 2.33 | T/T |
| 14 | 154 | 0.35 | 0.23 | 2.63 | 157 | 0.36 | 0.23 | 2.17 | C/T |
| 15 | 214 | 0.18 | 0.09 | 0.99 | 200 | 0.19 | 0.10 | 0.91 | — |
| 16 | 126 | 0.44 | 0.35 | 4.00 | 200 | 0.20 | 0.10 | 0.95 | C/C |
| 17 | 207 | 0.17 | 0.08 | 0.95 | 143 | 0.40 | 0.28 | 2.61 | T/T |
| 18 | 216 | 0.17 | 0.08 | 0.92 | 136 | 0.44 | 0.32 | 3.03 | T/T |
| 19 | 207 | 0.17 | 0.08 | 0.95 | 176 | 0.24 | 0.14 | 1.28 | T/T |
| 20 | 139 | 0.38 | 0.27 | 3.15 | 197 | 0.20 | 0.10 | 0.93 | C/C |
| 21 | 174 | 0.25 | 0.14 | 1.63 | 189 | 0.19 | 0.10 | 0.94 | C/C |
| 22 | 190 | 0.25 | 0.13 | 1.51 | 200 | 0.19 | 0.10 | 0.91 | C/C |
| 23 | 167 | 0.30 | 0.18 | 2.10 | 193 | 0.19 | 0.10 | 0.94 | C/C |
| 24 | 175 | 0.28 | 0.16 | 1.83 | 196 | 0.20 | 0.10 | 0.95 | C/C |
| 25 | 183 | 0.25 | 0.14 | 1.61 | 203 | 0.20 | 0.10 | 0.91 | C/C |
| 26 | 199 | 0.19 | 0.10 | 1.10 | 195 | 0.21 | 0.11 | 0.99 | — |
| 27 | 189 | 0.22 | 0.12 | 1.37 | 201 | 0.19 | 0.10 | 0.90 | C/C |
| 28 | 172 | 0.27 | 0.16 | 1.80 | 194 | 0.20 | 0.10 | 0.96 | C/C |
| 29 | 207 | 0.18 | 0.08 | 0.98 | 160 | 0.32 | 0.20 | 1.897 | T/T |
| 30 | 195 | 0.23 | 0.12 | 1.34 | 182 | 0.25 | 0.14 | 1.29 | C/T |
| 31 | 193 | 0.20 | 0.10 | 1.19 | 138 | 0.39 | 0.28 | 2.62 | T/T |
| 32 | 159 | 0.35 | 0.22 | 2.51 | 205 | 0.20 | 0.10 | 0.92 | C/C |

TABLE 4-continued

TDI assay data for diallelic marker DXS17

| | Rox-ddC | | | | Rox-ddU | | | | |
|---|---|---|---|---|---|---|---|---|---|
| Sample | FF | FR/RR | FE | $FE_s/FE_c$ | FF | FR/RR | FE | $FE_s/FE_c$ | Genotype |
| 33 | 209 | 0.18 | 0.09 | 0.99 | 155 | 0.32 | 0.21 | 1.94 | T/T |
| 34 | 213 | 0.17 | 0.08 | 0.94 | 142 | 0.39 | 0.27 | 2.54 | T/T |
| 35 | 139 | 0.38 | 0.27 | 3.17 | 167 | 0.21 | 0.13 | 1.19 | C/C |
| 36 | 212 | 0.18 | 0.08 | 0.96 | 136 | 0.41 | 0.30 | 2.83 | T/T |
| 37 | 190 | 0.19 | 0.10 | 1.16 | 158 | 0.23 | 0.14 | 1.35 | T/T |
| 38 | 165 | 0.33 | 0.20 | 2.31 | 158 | 0.34 | 0.22 | 2.04 | C/T |
| 39 | 209 | 0.18 | 0.08 | 0.98 | 146 | 0.30 | 0.27 | 2.50 | T/T |
| 40 | 155 | 0.33 | 0.21 | 2.43 | 151 | 0.35 | 0.23 | 2.18 | C/T |
| control 1 | 213 | 0.18 | 0.09 | | 193 | 0.21 | 0.11 | | |
| control 2 | 214 | 0.18 | 0.08 | | 196 | 0.20 | 0.10 | | |
| control 3 | 205 | 0.17 | 0.08 | | 192 | 0.20 | 0.10 | | |
| control 4 | 211 | 0.18 | 0.08 | | 193 | 0.20 | 0.11 | | |
| control 5 | 200 | 0.18 | 0.09 | | 189 | 0.20 | 0.11 | | |
| control 6 | 204 | 0.18 | 0.09 | | 190 | 0.21 | 0.11 | | |
| control 7 | 201 | 0.18 | 0.09 | | 188 | 0.19 | 0.10 | | |
| control 8 | 205 | 0.18 | 0.09 | | 188 | 0.21 | 0.11 | | |

TABLE 5

TDI assay data for diallelic marker D18S8

| | Rox-ddC | | | | Rox-ddU | | | | |
|---|---|---|---|---|---|---|---|---|---|
| Sample | FF | FR/RR | FE | $FE_s/FE_c$ | FF | FR/RR | FE | $FE_s/FE_c$ | Genotype |
| 1 | 231 | 0.30 | 0.13 | 1.35 | 238 | 0.36 | 0.15 | 1.19 | C/T |
| 2 | 185 | 0.37 | 0.20 | 2.09 | 235 | 0.28 | 0.12 | 0.96 | C/C |
| 3 | 191 | 0.38 | 0.20 | 2.09 | 238 | 0.28 | 0.12 | 0.92 | C/C |
| 4 | 207 | 0.33 | 0.16 | 1.66 | 230 | 0.29 | 0.12 | 0.99 | C/C |
| 5 | 1888 | 0.40 | 0.21 | 2.24 | 231 | 0.28 | 0.12 | 0.96 | C/C |
| 6 | 197 | 0.37 | 0.19 | 1.96 | 250 | 0.27 | 0.11 | 0.85 | C/C |
| 7 | 187 | 0.38 | 0.20 | 2.13 | 236 | 0.29 | 0.12 | 0.96 | C/C |
| 8 | 218 | 0.32 | 0.15 | 1.53 | 217 | 0.38 | 0.17 | 1.38 | C/T |
| 9 | 192 | 0.38 | 0.20 | 2.10 | 245 | 0.27 | 0.11 | 0.88 | C/C |
| 10 | 235 | 0.22 | 0.09 | 1.00 | 200 | 0.46 | 0.23 | 1.82 | T/T |
| 11 | 190 | 0.35 | 0.19 | 1.95 | 231 | 0.28 | 0.12 | 0.96 | C/C |
| 12 | 192 | 0.38 | 0.20 | 2.05 | 237 | 0.27 | 0.12 | 0.91 | C/C |
| 13 | 176 | 0.41 | 0.23 | 2.44 | 232 | 0.29 | 0.12 | 0.97 | C/C |
| 14 | 188 | 0.37 | 0.20 | 2.06 | 243 | 0.28 | 0.11 | 0.91 | C/C |
| 15 | 186 | 0.37 | 0.20 | 2.11 | 239 | 0.27 | 0.11 | 0.90 | C/C |
| 16 | 202 | 0.33 | 0.16 | 1.70 | 212 | 0.37 | 0.17 | 1.36 | C/T |
| 17 | 181 | 0.39 | 0.21 | 2.24 | 234 | 0.27 | 0.12 | 0.93 | C/C |
| 18 | 176 | 0.39 | 0.22 | 2.33 | 241 | 0.27 | 0.11 | 0.89 | C/C |
| 19 | 193 | 0.33 | 0.17 | 1.76 | 205 | 0.40 | 0.19 | 1.54 | C/T |
| 20 | 169 | 0.43 | 0.25 | 2.65 | 231 | 0.29 | 0.12 | 0.98 | C/C |
| 21 | 187 | 0.35 | 0.19 | 1.95 | 204 | 0.42 | 0.21 | 1.63 | C/T |
| 22 | 196 | 0.31 | 0.17 | 1.76 | 211 | 0.36 | 0.17 | 1.37 | C/T |
| 23 | 194 | 0.32 | 0.16 | 1.72 | 212 | 0.37 | 0.18 | 1.39 | C/T |
| 24 | 195 | 0.33 | 0.17 | 1.75 | 208 | 0.39 | 0.19 | 1.50 | C/T |
| 25 | 221 | 0.31 | 0.14 | 1.48 | 228 | 0.34 | 0.15 | 1.19 | C/T |
| 26 | 212 | 0.30 | 0.14 | 1.48 | 214 | 0.36 | 0.17 | 1.35 | C/T |
| 27 | 192 | 0.37 | 0.19 | 2.02 | 236 | 0.27 | 0.12 | 0.91 | C/C |
| 28 | 198 | 0.31 | 0.16 | 1.65 | 204 | 0.38 | 0.19 | 1.47 | C/T |
| 29 | 182 | 0.41 | 0.23 | 2.37 | 237 | 0.29 | 0.12 | 0.98.897 | C/C |
| 30 | 188 | 0.39 | 0.21 | 2.164 | 236 | 0.29 | 0.12 | 0.97 | C/C |
| 31 | 205 | 0.31 | 0.15 | 1.57 | 236 | 0.28 | 0.12 | 0.94 | C/C |
| 32 | 204 | 0.32 | 0.16 | 1.64 | 207 | 0.38 | 0.18 | 1.47 | C/T |
| 33 | 211 | 0.30 | 0.14 | 1.51 | 205 | 0.37 | 0.18 | 1.43 | C/T |
| 34 | 191 | 0.36 | 0.19 | 1.98 | 226 | 0.30 | 0.13 | 1.04 | C/C |
| 35 | 174 | 0.39 | 0.22 | 2.33 | 224 | 0.28 | 0.12 | 0.98 | C/C |
| 36 | 237 | 0.22 | 0.09 | 0.97 | 190 | 0.47 | 0.24 | 1.94 | T/T |
| 37 | 181 | 0.39 | 0.21 | 2.24 | 226 | 0.29 | 0.13 | 1.03 | C/C |
| 38 | 189 | 0.37 | 0.20 | 2.06 | 227 | 0.28 | 0.12 | 0.98 | C/C |
| 39 | 212 | 0.30 | 0.14 | 1.50 | 200 | 0.38 | 0.19 | 1.50 | C/T |
| 40 | 184 | 0.34 | 0.19 | 1.96 | 227 | 0.29 | 0.13 | 1.01 | C/C |
| control 1 | 235 | 0.22 | 0.09 | | 234 | 0.29 | 0.12 | | — |
| control 2 | 244 | 0.22 | 0.09 | | 243 | 0.29 | 0.12 | | — |
| control 3 | 234 | 0.22 | 0.09 | | 226 | 0.30 | 0.13 | | — |
| control 4 | 230 | .023 | 0.10 | | 230 | 0.29 | 0.13 | | — |
| control 5 | 232 | 0.23 | 0.10 | | 229 | 0.28 | 0.12 | | — |

TABLE 5-continued

TDI assay data for diallelic marker D18S8

| | Rox-ddC | | | | Rox-ddU | | | | |
|---|---|---|---|---|---|---|---|---|---|
| Sample | FF | FR/RR | FE | $FE_s/FE_c$ | FF | FR/RR | FE | $FE_s/FE_c$ | Genotype |
| control 6 | 231 | 0.22 | 0.10 | | 229 | 0.29 | 0.13 | | — |
| control 7 | 229 | 0.22 | 0.10 | | 227 | 0.29 | 0.13 | | — |
| control 8 | 228 | 0.22 | 0.10 | | 222 | 0.29 | 0.13 | | — |

All but two of the forty samples tested for the DXS17 locus provided definitive genotypes with the positive threshold set at $FE_{sample}/FE_{control}$ greater than 1.25. The two samples which yielded no definitive genotypes were analyzed by agarose gel electrophoresis and were shown to have very weak product bands, indicating suboptimal PCR amplification as the reason for this result. However, all D18S8 locus DNA samples were amplified successfully. All forty D18S8 samples provided definitive genotypes when the positive threshold is set at $FE_{sample}/FE_{control}$ greater than 1.15.

Figure 5:
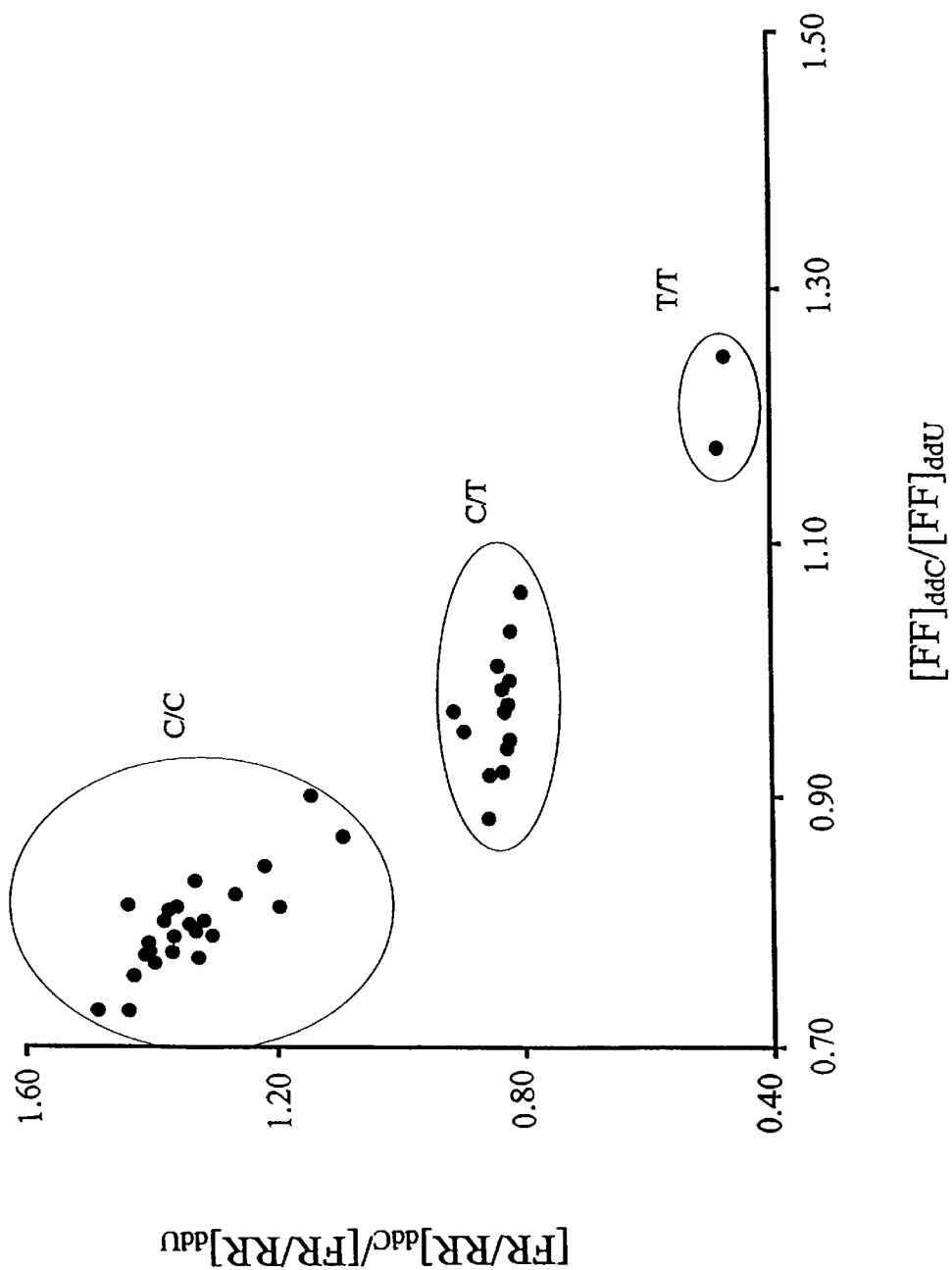
FIG. 5 illustrates the results of a template directed nucleotide incorporation assay detecting sequence tagged site D18S8 alleles as a distribution of points after plotting enhanced emission ratios of acceptor fluorophores against the donor fluorophore emission intensity ratios.

The D18S8 results were also analyzed by plotting the enhanced emission ratio of a sample in one allelic reaction over that for the same sample in the other allelic reaction against the fluorescein emission intensity ratios in the same reactions and are shown in FIG. 5. The homozygous and heterozygous alleles segregate into three groups with the homozygous thymidine samples identified using dideoxyuridine incorporation occupying the lower right corner of the plot, the homozygous cytosine samples in the upper left corner, and the heterozygotes in the center. External controls are not required when this type of plot is used.

EXAMPLE 3

This example illustrates the identification of a RET oncogene mutation in individual PCR amplified human DNA samples in a template directed nucleotide incorporation assay.

Heterozygous carriers of a single mutant RET allele are at high risk for developing multiple endocrine neoplasia, type 2 (MEN2), or familial medullary thyroid carcinoma (FMTC). Over twenty different single base-pair mutations in the RET oncogene have been found in families with MEN2/FMTC and the majority of these mutations are found in exons 10 and 11. The largest group of MEN2 families in our samples are affected by a change in codon 634 of exon 11. The mutation changes a cysteine codon (TGC) to a phenylalanine codon (TTC). A template directed nucleotide incorporation assay was used to detect the presence of the normal cysteine and the mutant phenylalanine codons in human DNA samples.

The PCR primers and fluorescein labeled template dependent nucleotide incorporation assay polynucleotide used to detect the MEN2C634F allele are shown in Table 6.

TABLE 6

| Primer | Sequence[1] | Annealing Temp. | SEQ ID NO: |
|---|---|---|---|
| MEN11p1 | 5'-cctctgcggtgccaagcctc | — | 16 |
| MEN11p2 | 5'-caccggaagaggagtagctg | — | 17 |
| MENC634F | 5'-F[1]-ccactgtgcgacgagctgt | 60° C. | 18 |

[1]Fluorescein

PCR reactions for amplification of target template DNA were prepared as in Example 2 with the following exceptions. The PCR primers MEN11p1 (SEQ ID:16) and MEN11p2 (SEQ ID:17) were used to amplify a 234 base pair product from exon 11 of the RET oncogene. The annealing and extension temperature was maintained at 60° C. for the first ten cycles and at 53° C. for the last thirty cycles.

30 μl of an enzymatic cocktail containing 5U shrimp alkaline phosphatase (Amersham), 2.5 U exonuclease I (Amersham), and 5 μl of 10× shrimp alkaline phosphatase (SAP) buffer (200 mM Tris HCl, pH 8.0, 100 mM $MgCl_2$) was added to 20 μl of each PCR reaction mixture to degrade excess polynucleotides and dephosphorylate excess deoxynucleoside triphosphates. Each mixture was incubated at 37° C. for thirty minutes before heat inactivation at 95° C. for fifteen minutes. The samples were maintained at 4° C. until used in the template directed nucleotide incorporation assay without further quantitation or characterization.

Reaction mixtures containing 60 nM of the RET oncogene fluorescein-labeled polynucleotide primer MENC634F (SEQ ID:18) and an appropriate 6-carboxy-X-rhodamine conjugated dideoxynucleoside triphosphate were mixed with 10 μl of each enzymatically treated PCR product, thermally cycled, and terminated as in example 1, except that the annealing temperature was set at 60° C.

The bases to be discriminated lie immediately 3' of the fluorescein-labeled polynucleotide. Therefore, two reactions were prepared. One reaction contained 6-carboxy-X-rhodamine conjugated dideoxyguanidine and the other reaction contained 6-carboxy-X-rhodamine conjugated dideoxyuridine.

After the reactions were completed, samples were transferred to microplates, denatured, and fluorescence enhancement was determined as in Example 2. All tests were completed in duplicate and the results were then compared to those obtained by the DNA Diagnostic Laboratory (Washington University, St. Louis, Mo.) using the same PCR amplified alleles to which restriction fragment length polymorphism analysis (RFLP) is applied using the restriction endonuclease BsoF1. The results of the assay for twenty-nine individuals from these families are shown in Table 7.

TABLE 7

TDI Assay Results for Mutation MENC634F

| | $FE_{sample}/FE_{control}$ | | Expected | Observed |
|---|---|---|---|---|
| Sample I.D. | ddG | ddT | Genotype | Genotype |
| 93-739 | 1.27 | 1.29 | G/T | G/T |
| 94-740 | 2.16 | 0.91 | G/G | G/G |
| 94-744 | 2.04 | 0.94 | G/G | G/G |
| 94-745 | 1.32 | 1.37 | G/T | G/T |
| 94-775 | 1.35 | 1.48 | G/T | G/T |
| 94-776 | 1.33 | 1.49 | G/G | G/G |
| 94-777 | 2.24 | 0.89 | G/T | G/T |
| 94-778 | 2.28 | 0.91 | G/G | G/G |
| 95-100 | 1.32 | 1.58 | G/T | G/T |
| 95-101 | 1.37 | 1.59 | G/T | G/T |
| 95-102 | 1.29 | 1.53 | G/T | G/T |
| 95-103 | 1.35 | 1.48 | G/T | G/T |
| 95-104 | 1.37 | 1.36 | G/T | G/T |
| 95-105 | 1.31 | 1.47 | G/T | G/T |
| 95-106 | 1.32 | 1.39 | G/T | G/T |
| 95-107 | 1.31 | 1.53 | G/T | G/T |
| 95-108 | 1.34 | 1.55 | G/T | G/T |
| 95-109 | 1.91 | 1.08 | G/G | G/G |
| 95-110 | 1.33 | 1.41 | G/T | G/T |
| 95-111 | 1.31 | 1.54 | G/T | G/T |
| 95-112 | 1.31 | 1.45 | G/T | G/T |
| 95-113 | 2.30 | 0.91 | G/G | G/G |
| 95-114 | 1/35 | 1.52 | G/T | G/T |
| 95-115 | 2.34 | 0.88 | G/G | G/G |
| 95-116 | 2.29 | 0.93 | G/G | G/G |
| 95-117 | 1.35 | 1.59 | G/T | G/T |
| 95-118 | 1.34 | 1.62 | G/T | G/T |
| 95-119 | 2.28 | 0.92 | G/G | G/G |
| 95-120 | 2.46 | 0.93 | G/G | G/G |

There are three results that may be expected when screening for this particular allelic mutation. Normal homozygous alleles each contain guanidine at the target position. Heterozygous individuals contain one normal and one mutant allele, indicated by the presence of a normal guanidine at one target position, and a thymidine in the other. The other expected genotype is also a homozygous individual in which both alleles are mutant and contain thymidine at the target position. The results show that these alleles are easily discriminated using the template directed nucleotide incorporation assay. The expected genotype from each allele matched the genotype observed using the PCR-RFLP method.

EXAMPLE 4

This example illustrates the identification of a three base mutation in the human cystic fibrosis gene using one fluorophore-labeled dideoxynucleoside triphosphate in a single sample using the template directed nucleotide incorporation assay.

Seventy percent of cystic fibrosis patients have a three base pair deletion in exon 5 of the cystic fibrosis gene (CF508). The carrier rate of this mutation is about five percent in the Caucasian population. Thirty-eight individuals from families with cystic fibrosis provided blood, from which DNA was obtained. These DNA samples were tested for the presence of the CF508 mutation in the cystic fibrosis gene. The PCR primers and fluorescein labeled template directed nucleotide incorporation assay polynucleotide used to detect the CF508 allele are shown in Table 8. The PCR primers CF508p1 (SEQ ID:19) and CF508p2 (SEQ ID:20) were used as in example 2 to amplify a 578 base pair segment from exon 5 of the cystic fibrosis gene in DNA from each of these thirty-eight individual patients. The PCR product is useful in testing for the presence of the unique three base pair deletion.

TABLE 8

| Primer | Sequence | Annealing Temp. | SEQ ID NO: |
|---|---|---|---|
| CF508p1 | 5'-gtgcatagcagagtacctgaaacaggaagta | — | 19 |
| CF508p2 | 5'-tgatccattcacagtagcttacccatagagg | — | 20 |
| CF508F25 | 5'-F[1]-ctggcaccattaaagaaaatatcat | 50° C. | 21 |

[1]Fluorescein.

The bases to be discriminated in carriers of the CF508 allele are known from DNA sequence analysis to be either a cytosine or a thymidine. These lie immediately 3' of the fluorescein-labeled polynucleotide, CF508F25 (SEQ ID:21), when hybridized to the template nucleotide sequence. Separate reactions were used, each containing only one fluorophore-labeled dideoxynucleoside triphosphate, to determine the presence or absence of the CF508 mutation in each DNA sample. PCR amplified DNA samples were subjected to a template directed nucleotide incorporation assay without further purification of products after treatment with shrimp alkaline phosphatase and exonuclease III as in example 3. Template directed nucleotide incorporation reaction conditions were as in example 3, except that each reaction contained either 6-carboxy-X-rhodamine conjugated dideoxycytosine or 6-carboxy-X-rhodamine conjugated dideoxyuridine. Therefore, individual reactions were carried out to distinguish the presence or absence of the respective alleles.

Figure 6:
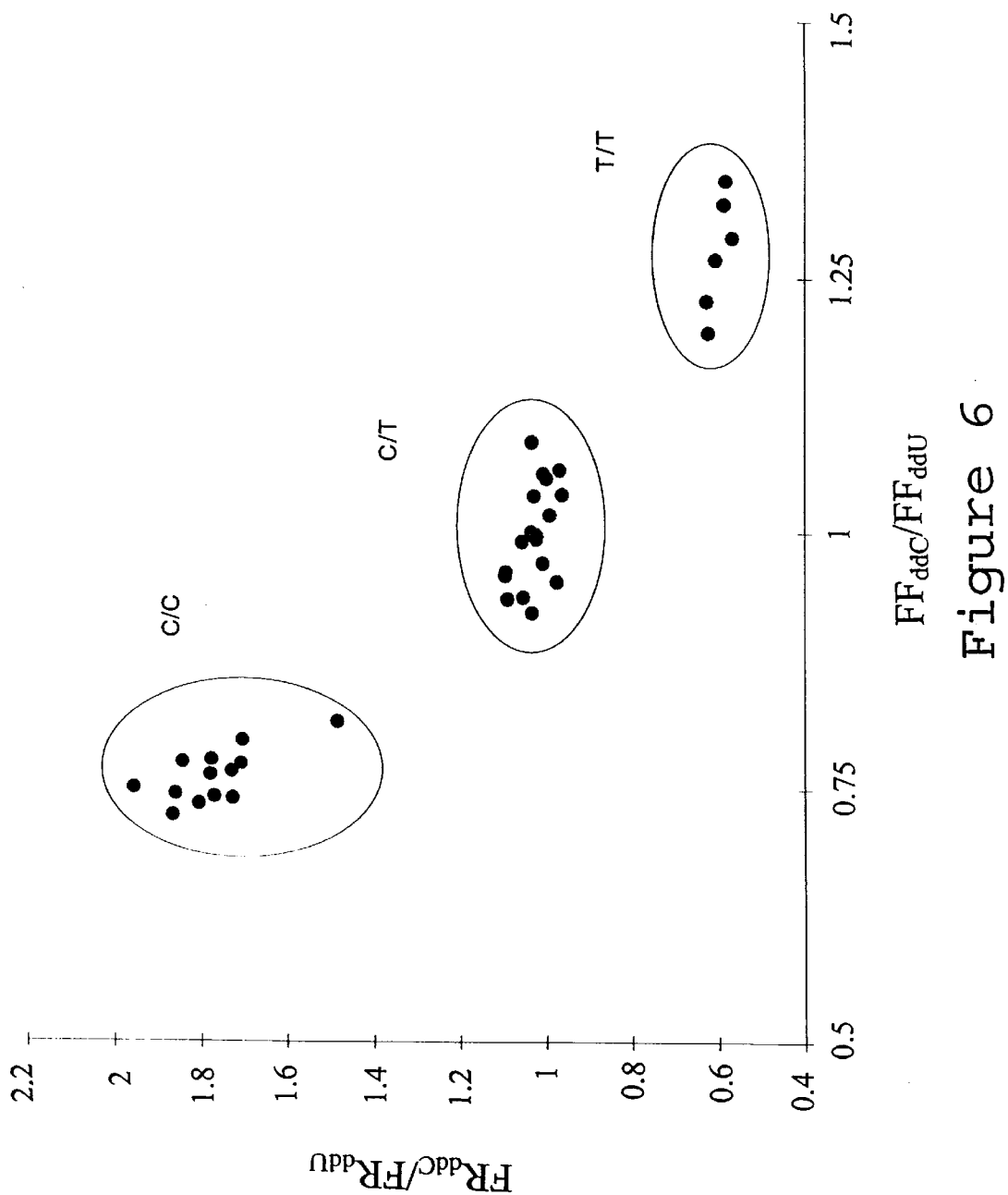
FIG. 6 illustrates the results of a template directed nucleotide incorporation assay detecting a cystic fibrosis allele as a distribution of points after plotting enhanced emission ratios of acceptor fluorophores against the donor fluorophore emission intensity ratios.

The results are shown in FIG. 6 after plotting the enhanced emission ratios of each allelic reaction as in example 2 and show a distribution of data points similar to those observed in FIG. 5. The homozygous and heterozygous alleles segregate into three groups with the homozygous thymidine samples identified using dideoxyuridine incorporation occupying the lower right corner of the plot, the homozygous cytosine samples in the upper left corner, and the heterozygotes in the center.

EXAMPLE 5

This example illustrates the identification of a three base mutation in exon 5 of the cystic fibrosis gene using two different fluorophore-labeled dideoxynucleoside triphosphates in a single sample using the template directed dideoxynucleotide incorporation assay.

The PCR amplified, phosphatase and exonuclease treated DNA samples used in example 4 were subjected to a template directed nucleotide incorporation assay. The presence of wild type and mutant CF508 alleles were detected in single reaction volumes for each patient DNA sample. Thus, each individual template dependent nucleotide incorporation assay contained 6-carboxy-X-rhodamine conjugated dideoxycytosine and tetramethyl-6-carboxyrhodamine conjugated dideoxyuridine as acceptor fluorophore-conjugated dideoxynucleoside triphosphates. Template directed nucleotide incorporation assays were completed as in example 4, and the fluorescence emission of the fluorophores was determined using an LS-50B spectrometer.

Fluorescein emission of each sample ($FF_{obs}$) was determined by exciting the sample at 488 nm with a slit width of 5 mm and detecting the emission at 515 nm with a slit width of 4 mm. 6-carboxy-X-rhodamine emission ($RR_{obs}$) was determined by exciting the sample at 580 nm with a slit width of 5 mm and detecting the emission at 605 nm with a slit width of 6 mm. Tetramethyl-6-carboxyrhodamine ($TT_{obs}$) emission was determined by exciting the sample at 547 nm with a slit width of 5 mm and detecting the emission at 583 nm with a slit width of 6 mm. The enhanced emission due to energy transfer was determined for 6-carboxy-X-rhodamine ($FR_{obs}$) by exciting the sample as 488 nm with a slit width of 5 mm and detecting the emission at 605 nm. Tetramethyl-6-carboxyrhodamine enhanced emission due to energy transfer ($FT_{obs}$) was determined by exciting the sample at 488 nm and detecting the emission at 583 nm.

A matrix was constructed using single fluorophores in order to analyze the data. As an example, the FR reading represents the fraction of fluorescein emission ($FR_f$) when only fluorescein is present in the system. Similarly, $FR_r$ is defined as the tetramethyl-6-carboxyrhodamine contribution to FR in the presence of only tetramethyl-6-carboxyrhodamine (TAMRA). $FT_f$ and $FT_r$ represent the contributions of fluorescein and 6-carboxy-X-rhodamine (ROX) to FT. The matrix is shown in Table 9.

TABLE 9

| Readings | Fluorophore Present | | |
|---|---|---|---|
| | Fluorescein | ROX | TAMRA |
| FF | 1.0000 | 0.0000 | 0.0000 |
| FR | 0.1255 | 0.0549 | 0.0409 |
| FT | 0.2254 | 0.0074 | 0.0480 |
| RR | 0.0000 | 1.0000 | 0.2252 |
| TT | 0.0000 | 0.1286 | 1.0000 |

The above values are used to determine if a sample is positive or negative using the following formulas.

$FR_{corrected} = FR_{obs} - FR_f - FR_t = FR_{obs} - 0.1255 FF_{obs} - 0.0409 TT_{obs}$ $FT_{corrected} = FT_{obs} - FT_f - FT_r = FT_{obs} - 0.2254 FF_{obs} - 0.0074 RR_{obs}$ $RR_{corrected} = RR_{obs} - RR_t = RR_{obs} - 0.2252 TT_{obs}$ $TT_{corrected} = TT_{obs} - TT_r = TT_{obs} - 0.1286 RR_{obs}$ The corrected FR and FT values are used to calculate fluorescence enhancement (FE). A sample is scored as positive if the fluorescence enhancement value of the sample ($FE_{sample}$) is greater than the sum of the fluorescence enhancement value of the control ($FE_{control}$) and seven standard deviations of the controls and represented by the following formula:

$FE_{sample} > FE_{control} + (6.95 \times \text{Standard deviation}_{control})$.

The results for the assay detecting the cystic fibrosis allele are shown in Table 10. There are three results that may be expected using this particular allelic mutation. Normal homozygous individuals have cytosine at the same position in both alleles. The presence of a cytosine in one allele and a thymidine in another indicates a heterozygous carrier. The only other allele type expected is a homozygous cystic fibrosis affected individual in which both alleles contain a thymidine, indicating that both alleles contain the three base pair deletion. The results show that these alleles are easily discriminated using this method. The expected genotype from each allele matched perfectly with the observed genotype.

Fluorescence intensity was also monitored during thermo cycling using an Applied Biosystems Incorporated Sequence Detection System 7700 (Perkin/Elmer) and the accompanying ABI 7700 software to do the analysis and export the multicomponent data as shown in Table 11. This data contains the intensity changes for fluorescein, tetramethyl-6-carboxyrhodamine, and 6-carboxy-X-rhodamine along with the standard deviation for each well. For a positive reaction, the intensity of 6-carboxy-X-rhodamine should be increasing over 200 units, and that of tetramethyl-6-carboxyrhodamine should be increasing over 100 units. Because the fluorescent intensities are monitored along with the reaction, the change of intensity along the reaction is adequate to determine whether reaction is positive or negative.

TABLE 10

Two Acceptor TDI Assay:
Results for Cystic Fibrosis Samples

| Sample I.D. | $FE_{sample}/FE_{control}$ | | Expected | Observed |
| | Rox-ddC | Tamra-ddU | Genotype | Genotype |
|---|---|---|---|---|
| 93-014 | 1.24 | 2.12 | C/T | C/T |
| 93-019 | 1.19 | 2.15 | C/T | C/T |
| 93-21c | 1.21 | 2.22 | C/T | C/T |
| 94-015 | 1.23 | 1.01 | C/C | C/C |
| 94-018 | 1.20 | 2.24 | C/T | C/T |
| 94-022 | 1.27 | 1.07 | C/C | C/C |
| 94-023 | 1.28 | 1.11 | C/C | C/C |
| 94-024 | 1.25 | 0.88 | C/C | C/C |
| 94-151 | 1.18 | 2.13 | C/T | C/T |
| 94-152 | 1.21 | 1.98 | C/T | C/T |
| 94-217 | 1.07 | 2.65 | T/T | T/T |
| 94-417 | 1.29 | 0.98 | C/C | C/C |
| 94-528 | 1.05 | 2.46 | T/T | T/T |
| 95-049 | 1.10 | 2.48 | T/T | T/T |
| 95-093 | 1.22 | 1.94 | C/T | C/T |
| 95-167 | 1.23 | 2.15 | C/T | C/T |
| 95-182 | 1.21 | 2.26 | C/T | C/T |
| 95-184 | 1.17 | 2.28 | C/T | C/T |
| 95-241 | 1.18 | 1.98 | C/T | C/T |
| 95-262 | 1.04 | 2.59 | T/T | T/T |
| 95-291 | 1.20 | 1.93 | C/T | C/T |
| 95-316 | 1.18 | 2.09 | C/T | C/T |
| 95-615 | 1.26 | 3.99 | C/T | C/T |
| 95-808 | 1.19 | 2.05 | C/T | C/T |
| 95-897 | 1.22 | 2.03 | C/T | C/T |
| 95-898 | 1.09 | 2.83 | T/T | T/T |
| 95-1005 | 1.08 | 2.72 | T/T | T/T |
| 96-0344 | 1.20 | 2.14 | C/T | C/T |

TABLE 11

Two Acceptor TDI Assay:
Results from PE7700

| Sample | FF | FR | FT | FF | FR | FT | FF | FR | FT | Expected | Genotype |
|---|---|---|---|---|---|---|---|---|---|---|---|
| 93-014 | 5028 | 980 | 1134 | 2610 | 1838 | 1337 | 2106 | 2189 | 1429 | C/T | C/T |
| 94-025 | 4549 | 885 | 1070 | 2530 | 1940 | 1058 | 2170 | 2315 | 1078 | C/C | C/C |
| 94-330 | 3120 | 651 | 885 | 1581 | 1240 | 873 | 1408 | 1402 | 892 | C/C | C/C |
| 95-182 | 3902 | 708 | 1092 | 1994 | 1256 | 1226 | 1590 | 1488 | 1298 | C/T | C/T |
| 95-808 | 4000 | 717 | 1105 | 2568 | 1048 | 1181 | 2140 | 1342 | 1256 | C/T | C/T |
| 93-019 | 3916 | 729 | 1030 | 2101 | 1284 | 1144 | 1752 | 1549 | 1207 | C/T | C/T |
| 94-202 | 5312 | 1025 | 1305 | 2983 | 1762 | 1184 | 1910 | 1860 | 1017 | C/C | C/C |
| 94-488 | 4925 | 1024 | 1041 | 3109 | 1565 | 979 | 2794 | 1895 | 989 | C/C | C/C |
| 94-217 | 4550 | 970 | 991 | 2159 | 1101 | 1196 | 1880 | 1200 | 1273 | T/T | T/T |
| 94-528 | 4914 | 991 | 1350 | 2173 | 1135 | 1682 | 1810 | 1239 | 1810 | T/T | T/T |

EXAMPLE 6

This example illustrates the identification of a single base change in target DNA molecules in a polynucleotide ligation assay using fluorescence enhancement.

s14102 (Genbank accession number L33276) is a 217 base pair human sequence tagged site containing a known single nucleotide polymorphism. A set of four 40-mers comprised of an identical sequence except for the base at position twenty-one and corresponding to the DNA sequence flanking the known SNP site were synthesized as in example 1. Each of the four possible bases A, C, G, or T were uniquely represented in each of the four different 40-mer templates as shown in Table 2. Allele specific polynucleotides containing Texas Red or rhodamine as the acceptor fluorophore at various positions and 5' phosphorylated polynucleotides containing fluorescein as the donor fluorophore at various positions were prepared as in example 1. The DNA sequence of the donor and allele specific acceptor polynucleotides corresponds to the complementary sequence of the template molecule and are shown in Table 12.

TABLE 12

| Oligomer | Nucleotide Sequence | SEQ ID NO: |
|---|---|---|
| Donor Sequence | 5'-TTGTTTTATTTTTGTAAAAT | 22 |
| Acceptor Sequence-A | 5'-TTTATGGCTTAGTGGTTTCA | 23 |
| Acceptor Sequence-G | 5'-TTTATGGCTTAGTGGTTTCG | 24 |
| s14102p1 | 5'-CAGTATGCTCACTAAAGCC | 25 |
| s14102p2 | 5'-CTCATATTCACATCTCTCCG | 26 |

Donor polynucleotides were additionally labeled with digoxigenin using dig-11-deoxyuridine triphosphate and terminal transferase according to the manufacturers instructions (Boehringer Mannheim Biochemicals, Indianapolis, Ind.). 1 pM of 40 mer template was used in each reaction. In other reactions, the gel purified 217 bp PCR product generated using the s14102 PCR primers (SEQ ID:25, SEQ ID:26) in a 20 µl reaction was used as a template. An allele specific acceptor polynucleotide labeled with Texas Red at position 16, 5 nucleotide 5' to the site of ligation, was incubated with a donor polynucleotide labeled with fluorescein at position 5, 5 nucleotides 3' to the site of ligation and 3' end labeled with digoxygenin conjugated deoxyuridine triphosphate in the presence of a 40-mer template with a one-base mismatch or with a 40-mer template that was perfectly complementary to the donor and acceptor polynucleotides. Ligation reactions contained 5 pM each of the polynucleotide ligation assay specific primers and Ampligase thermostable DNA ligase (Epicenter Technologies, Madison, Wis.) in a buffer supplied by the manufacturer. The primer/ligase mixture was added to the template in a 20 µl reaction volume and subjected to thirty cycles of 94° C. denaturation for one minute followed by 45° C. annealing and ligation for five minutes. control reactions contained no Ampligase.

Figure 7A:
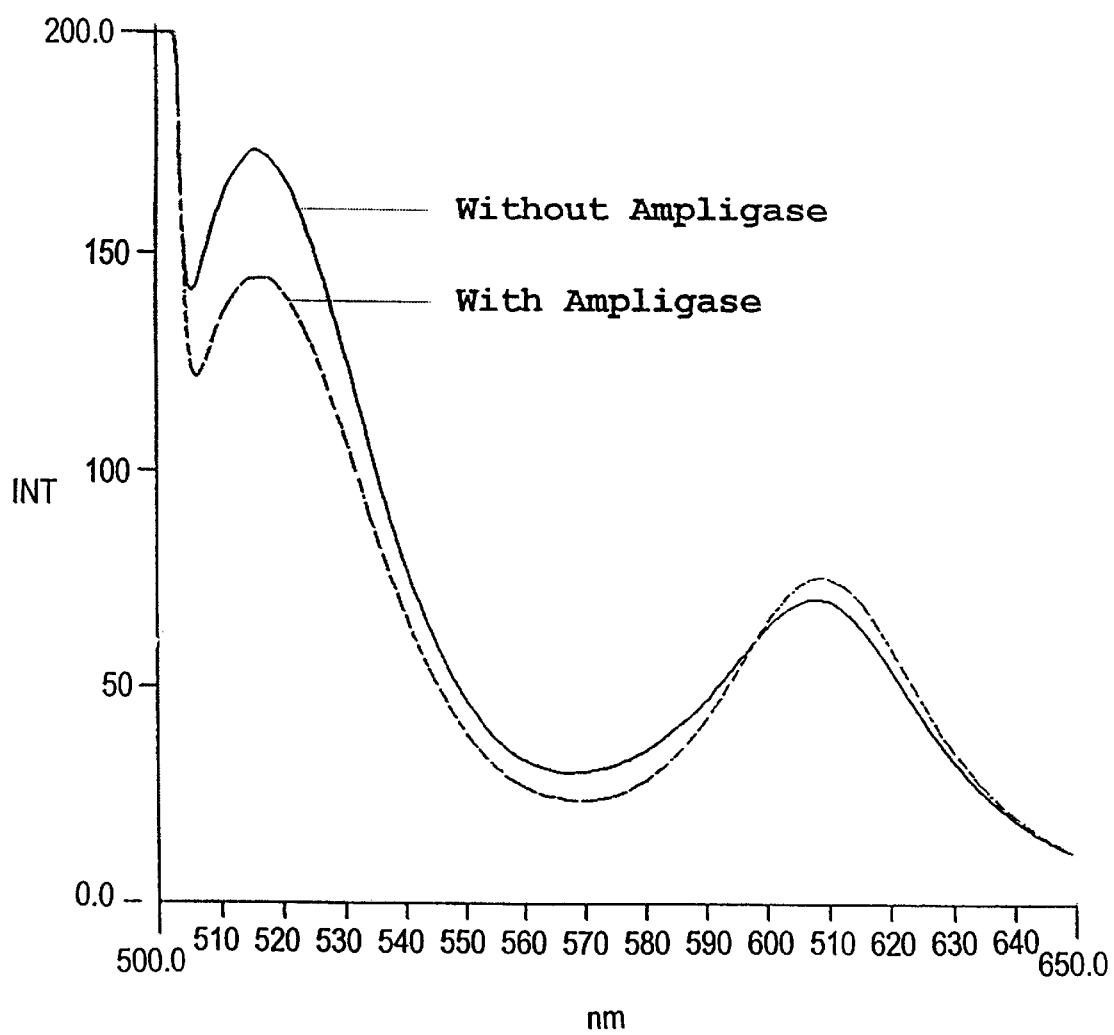
FIGS. 7A and B illustrate (a) the fluorescence emission spectra of template directed ligation assay products detected in the presence or absence of ligase; and (b) the same curve after subtracting the control emission spectra from that of the Ampligase positive sample.
Figure 7B:
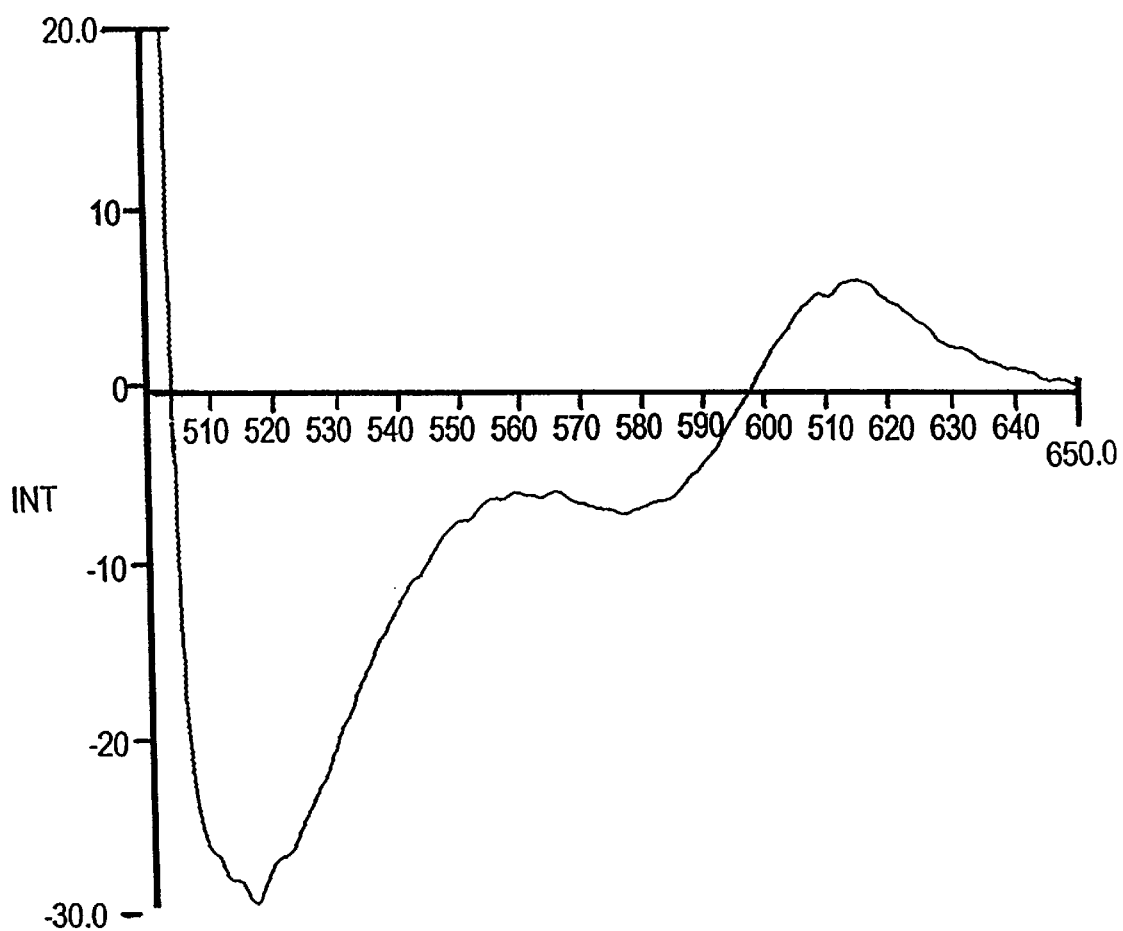

10 µl of each ligation reaction were denatured with 200 µl of 0.5 N NaOH and placed in a cuvette to obtain an emission spectrum excited at 490 nm using the LS-50B luminescence spectrometer (Perkin-Elmer, Norwalk, Conn.). Alternatively, the sample was denatured with 40 µl of 0.6 N NaOH and placed in a well of a white MicroFLUOR microtiter plate (Baxter, McGaw Park, Ill.) and read directly using the LS-50B spectrometer. Energy transfer between the two fluorophores was observed when the emission spectra of the reactions with the correct perfectly matched template were compared to those with the mismatched template. Energy transfer in the form of quenching of donor emission was much more pronounced than that due to the enhanced emission of the acceptor (FIG. 7). The ratio of the emission of acceptor to emission of donor (A/D) was used to establish whether energy transfer has occurred. The A/D of a control sample without ligase was used as the baseline to determine the A/D of the test samples to show that, in the presence of a perfectly matched template, A/D of the test sample is significantly larger than A/D of the control. A sample with the mismatched template shows an A/D similar to that of the no ligase control. When excited at 490 nm, the excitation maximum of the donor fluorescein, both quenching of the donor emission at 515 nm and enhanced emission of the acceptor Texas Red fluorescence at 610 nm were observed in the test sample when compared to the control sample (FIG. 7 A). The shape of the subtraction curve is characteristic of energy transfer (FIG. 7 B).

EXAMPLE 7

This example illustrates the identification of a single base change in PCR amplified human sequence tagged sites in a polynucleotide ligation assay using fluorescence enhancement.

The sequence tagged sites DXS17 and S14102 amplified as in examples 2 and 6 respectively. Allele specific polynucleotides 5' end labeled with Texas Red or rhodamine as the acceptor fluorophore and 5' phosphorylated polynucleotides 3' end labeled with fluorescein as the donor fluorophore were prepared as in example 6 and are shown in Table 13.

TABLE 13

| Oligomer | Nucleotide Sequence | SEQ ID NO: |
|---|---|---|
| DXS17 Allele A | 5'-ATTGGATTATTTGTAAACTCAAAGGATAAGTGCATAAAGGG | 27 |
| DXS17 Allele G | 5'-ATTGGATTATTTGTAAACTCGAAGGATAAGTGCATAAAGGG | 28 |
| DXS17 Common Probe | 5'-GAGTTTACAAATAACCAAT-F$^3$-3' | 29 |
| DXS17 Allelic Probe (1) | 5'-F$^1$-CCCTTTATGCACTTATCCTTT-3' | 30 |
| DXS17 Allelic Probe (2) | 5'-F$^2$-CCCTTTATGCACTTATCCTTC-3' | 31 |
| s14102 Allele T | 5'-ATTTTACAAAAATAAAACAATGAAACCACTAAGCCATAAA | 32 |
| s14102 Allele C | 5'-ATTTTACAAAAATAAAACAACGAAACCACTAAGCCATAAA | 33 |
| s14102 Common Probe | 5'-TTGTTTTATTTTTGTAAAAT-F$^3$-3' | 34 |
| S14102 Allelic Probe (1) | 5'-F$^1$-TTTATGGCTTTAGTGGTTTCA-3' | 35 |
| S14102 Allelic Probe (2) | 5'-F$^2$-TTTATGGCTTTAGTGGTTTCG-3' | 36 |

[1]Rhodamine
[2]Texas Red
[3]Fluorescein

Purified PCR products for each sequence tagged site from five individual samples were incubated in two parallel 20 μl reactions with 5 pM of 5' fluorescein-labeled common polynucleotide probe, 5 pM of one of the fluorophore-labeled allele-specific polynucleotide probes, and 2U Amp-ligase in a ligase buffer containing 20 mM Tris HCl, Ph 7.6, 150 mM KCl, 0.1% Triton X-100, 1 mM NAD, and 10 mM MgCl$_2$. Two control reactions without ligase were included for each sequence tagged site. Each reaction mixture was cycled sixty times using thermal conditions as in example 6. The reaction was terminated by adding 1.5 μl 0.5M EDTA, pH 8.0 and the products were denatured by addition of 50 μl 0.2 N NaOH.

Fluorescence intensities were determined using a fluorescent spectrophotometer as in example 6. Total donor emission ($D_f+D_b$) was measured by exciting each reaction mixture at 495 nm and measuring emission at 515 nm. Total acceptor emission ($A_f+A_b$) for rhodamine was measured by exciting at 547 nm and measuring emission at 572 nm, and for Texas Red by exciting at 589 nm and measuring emission at 615 nm. Enhanced fluorescence ($A_e$) was determined by exciting the reaction mixture at 495 nm and measuring emission at 572 nm for rhodamine and 615 nm for Texas Red.

Fluorescence enhancement (FE) was calculated by the formula FE=$[A_e/(A_f+A_b)]/(D_f+D_b)$. PCR products that do not contain the specific alleles served as controls. Samples were scored positive when $FE_{sample}>[FE_{control}+6.95\times \text{Standard Deviation}_{control}]$. This corresponds to a cutoff ratio for $FE_{sample}/FE_{control}$ of 1.25. The results are shown in Table 14. The assay correctly identified the alleles present in each sample.

TABLE 14

Oligonucleotide Ligation Assay Analysis of PCR Products with Known Genotype

| | | T Allele Probe (Rhodamine Label) | | | | | C Allele Probe (Texas Red Label) | | | | |
|---|---|---|---|---|---|---|---|---|---|---|---|
| Sample | Genotype | $A_e/[A_f + A_b]$ | $D_f + D_b$ | FE[1] | $FE_s/FE_c$ | Result[2] | $A_e/[A_f + A_b]$ | $D_f + D_b$ | FE[1] | $FE_s/FE_c$ | Result[2] |
| | | | | Marker - DXS17 | | | | | | | |
| 3 | C/C | 0.34 | 0.63 | 0.54 | 1.17 | − | 0.07 | 0.62 | 0.11 | 1.25 | + |
| 42 | T/T | 0.35 | 0.56 | 0.63 | 1.36 | + | 0.06 | 0.65 | 0.09 | 1.03 | − |
| 70 | T/T | 0.35 | 0.56 | 0.63 | 1.36 | + | 0.07 | 0.73 | 0.10 | 1.07 | − |
| 71 | C/C | 0.34 | 0.63 | 0.54 | 1.17 | − | 0.07 | 0.62 | 0.11 | 1.25 | + |
| 75 | T/T | 0.35 | 0.58 | 0.60 | 1.31 | + | 0.07 | 0.74 | 0.09 | 1.05 | − |
| Control | — | 0.34 | 0.72 | 0.47 | — | − | 0.07 | 0.77 | 0.09 | — | − |
| Control | — | 0.34 | 0.76 | 0.45 | — | − | 0.07 | 0.79 | 0.09 | — | − |

[1]The average FE of controls for the T Allele Probe is 0.4654 ± 0.018 and for the C Allele Probe is 0.09 ± 0.0013. $FE_s$ is fluorescence enhancement of sample and $FE_c$ the average value for control.
[2]Samples are scored positive if $FE_{sample} > [FE_{control} + 6.965 \times SD_{control}]$ which corresponds to a 99% confidence interval in the Students t-test.

| | | | | Marker - S14102 | | | | | | | |
|---|---|---|---|---|---|---|---|---|---|---|---|
| 1 | T/T | 0.42 | 1.58 | 0.27 | 1.30 | + | 0.06 | 1.79 | 0.03 | 1.12 | − |
| 2 | T/T | 0.41 | 1.46 | 0.28 | 1.37 | + | 0.06 | 1.84 | 0.03 | 1.09 | − |
| 4 | T/T | 0.41 | 1.60 | 0.26 | 1.25 | + | 0.06 | 1.85 | 0.03 | 1.08 | − |
| 6 | T/T | 0.41 | 1.54 | 0.27 | 1.30 | + | 0.06 | 1.87 | 0.03 | 1.07 | − |
| 9 | T/T | 0.41 | 1.58 | 0.26 | 1.27 | + | 0.06 | 2.09 | 0.03 | 0.965 | − |
| Control | — | 0.39 | 1.91 | 0.20 | — | − | 0.07 | 2.47 | 0.03 | — | − |
| Control | — | 0.39 | 1.83 | 0.21 | — | − | 0.07 | 2.33 | 0.03 | — | − |

[1]The average FE of controls for the T Allele Probe is 0.2028 ± 0.0134 and for the C Allele Probe is 0.0287 ± 0.0018. $FE_s$ is fluorescence enhancement of sample and $FE_c$ the average value for control.
[2]Samples are scored positive if $FE_{sample} > [FE_{control} + 6.965 \times SD_{control}]$ which corresponds to a 99% confidence interval in the Students t-test.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A kit for detecting the presence of a target site of at least one nucleotide in a nucleic acid, the kit comprising:
   (a) a polynucleotide covalently linked to one fluorophore and capable of binding to the target site or immediately 3' to the target site; and
   (b) a dideoxynucleotide covalently linked to a second fluorophore, which is capable of binding to the nucleic acid immediately 5' to the polynucleotide and capable of adding by 3' extension to the polynucleotide, wherein the emission spectrum of one of the fluorophores overlaps the excitation spectrum of the other, packaged in a container.

2. The kit according to claim 1 wherein one fluorophore is selected from the group consisting of fluorescein, cascade blue, 4,4-difluoro-5,7-diphenyl-4-bora-3a,4a-diaza-s-indacene-3-propionic acid, 4,4-difluoro-5,p-methoxyphenyl-4-bora-3a,4a-diaza-s-indacene-3-propionic acid and 4,4-difluoro-5-styryl-4-bora-3a,4a-diaza-S-indacene-propionic acid and the other fluorophore is selected from the group consisting of 6-carboxy-X-rhodamine, N,N,N',N'-tetramethyl-6-carboxyrhodamine, Texas Red, Eosin, fluorescein, 4,4-difluoro-5,7-diphenyl-4-bora-3a,4a-diaza-s-indacene-3-propionic acid, 4,4-difluoro-5,p-methoxyphenyl-4-bora-3a,4a-diaza-s-indacene-3-propionic acid and 4,4-difluoro-5-styryl-4-bora-3a,4a-diaza-S-indacene-propionic acid.

3. The kit according to claim 2 wherein one fluorophore is fluorescein and the other fluorophore is 6-carboxy-X-rhodamine or N,N,N',N'-tetramethyl-6-carboxyrhodamine.

4. A kit for detecting the presence of a target site of at least one nucleotide in a nucleic acid, the kit comprising:
   (a) a first polynucleotide covalently linked to a first fluorophore; and
   (b) a second polynucleotide covalently linked to a second fluorophore wherein the second polynucleotide is capable of being ligated to the first polynucleotide to form an oligonucleotide which binds to the target site, wherein the emission spectrum of one of the fluorophores overlaps the excitation spectrum of the other, packaged in a container.

5. The kit according to claim 3 wherein the first fluorophore is selected from the group consisting of fluorescein, cascade blue, 4,4-difluoro-5,7-diphenyl-4-bora-3a,4a-diaza-s-indacene-3-propionic acid, 4,4-difluoro-5,p-methoxyphenyl-4-bora-3a,4a-diaza-s-indacene-3-propionic acid and 4,4-difluoro-5-styryl-4-bora-3a,4a-diaza-S-indacene-propionic acid and the other fluorophore is selected from the group consisting of 6-carboxy-X-rhodamine, N,N,N',N'-tetramethyl-6-carboxyrhodamine, Texas Red, Eosin, fluorescein, 4,4-difluoro-5,7-diphenyl-4-bora-3a,4a-diaza-s-indacene-3-propionic acid, 4,4-difluoro-5,p-methoxyphenyl-4-bora-3a,4a-diaza-s-indacene-3-propionic acid and 4,4-difluoro-5-styryl-4-bora-3a,4a-diaza-S-indacene-propionic acid.

6. The kit according to claim 5 wherein one fluorophore is fluorescein and the other fluorophore is Texas Red.

7. The kit of claim 1, wherein the fluorophore that is linked to the polynucleotide is separated by at least about 20 nucleotides from the fluorophore that is linked to the dideoxynucleotide after the dideoxynucleotide has been added by 3' extension to the polynucleotide.

8. The kit of claim 7, wherein the fluorophore that is linked to the polynucleotide is separated by at least about 40 nucleotides from the fluorophore that is linked to the dideoxynucleotide after the dideoxynucleotide has been added by 3' extension to the polynucleotide.

9. The kit of claim 4 wherein the first fluorophore that is linked to the first polynucleotide is separated by at least about 20 nucleotides from the second fluorophore that is linked to the second polynucleotide after the second polynucleotide has been added by 3' extension to the first polynucleotide.

10. The kit of claim 9 wherein the first fluorophore that is linked to the first polynucleotide is separated by at least about 40 nucleotides from the second fluorophore that is linked to the second polynucleotide after the second polynucleotide has been added by 3' extension to the first polynucleotide.

* * * * *